(12) United States Patent
Szente

(10) Patent No.: US 10,610,524 B2
(45) Date of Patent: Apr. 7, 2020

(54) CELLULAR HYDRATION COMPOSITIONS

(71) Applicant: Eastpond Laboratories Limited, Douglas (IM)

(72) Inventor: Lajos Szente, Budapest (HU)

(73) Assignee: Eastpond Laboratories Limited, Douglas (IM)

( * ) Notice: Subject to any disclaimer, the term of this patent is extended or adjusted under 35 U.S.C. 154(b) by 0 days.

(21) Appl. No.: 14/932,929

(22) Filed: Nov. 4, 2015

(65) Prior Publication Data

US 2016/0067343 A1    Mar. 10, 2016

Related U.S. Application Data

(63) Continuation of application No. 12/983,234, filed on Dec. 31, 2010, now abandoned.

(51) Int. Cl.
*A61K 9/00* (2006.01)
*A61K 47/40* (2006.01)
(Continued)

(52) U.S. Cl.
CPC .............. *A61K 31/455* (2013.01); *A23L 2/38* (2013.01); *A23L 2/52* (2013.01); *A23L 2/56* (2013.01);
(Continued)

(58) Field of Classification Search
None
See application file for complete search history.

(56) References Cited

U.S. PATENT DOCUMENTS 5,221,735 A    6/1993  Leuenberger et al.
5,552,378 A    9/1996  Trinh et al.
(Continued)

FOREIGN PATENT DOCUMENTS

CN    101501052 A    8/2009
EP    0406811 A2    1/1991
(Continued)

OTHER PUBLICATIONS

Williams et al. European Journal of Pharmaceutics and Biopharmaceutics 46 (1998) 355-360.*
(Continued)

*Primary Examiner* — Julie Wu
*Assistant Examiner* — Douglas F White
(74) *Attorney, Agent, or Firm* — Kolisch Hartwell, P.C.

(57) ABSTRACT

A composition interacts with a biological cell system that includes bioactive molecules with biomolecular surfaces, cellular components and water molecules with a specific density. The composition includes a biologically active component that is constructed to increase an activity of a biological cell system by increasing the hydration of one or more components of that cell system. The biologically active component may include a primary carbohydrate clathrate subcomponent that increases the H-bonded structure of water, and a secondary solute subcomponent. The biologically active component may include an inclusion complex that is made up of a clathrate component and a complex-forming compound. The clathrate subcomponent may include amyloses or cyclodextrins. There is also a beverage and a method that improves cellular hydration in an animal, such as a human.

8 Claims, 18 Drawing Sheets

(51) Int. Cl.
*A61K 31/455* (2006.01)
*A23L 2/38* (2006.01)
*C08L 5/16* (2006.01)
*A61K 47/61* (2017.01)
*A61K 31/198* (2006.01)
*A23L 33/175* (2016.01)
*A23L 33/15* (2016.01)
*A23L 29/212* (2016.01)
*A23L 2/66* (2006.01)
*A23L 2/58* (2006.01)
*A23L 2/56* (2006.01)
*A23L 2/52* (2006.01)

(52) U.S. Cl.
CPC .................. *A23L 2/58* (2013.01); *A23L 2/66* (2013.01); *A23L 29/212* (2016.08); *A23L 33/15* (2016.08); *A23L 33/175* (2016.08); *A61K 9/0095* (2013.01); *A61K 31/198* (2013.01); *A61K 47/61* (2017.08); *C08L 5/16* (2013.01); *A23V 2002/00* (2013.01)

(56) References Cited

U.S. PATENT DOCUMENTS

| | | | |
|---|---|---|---|
| 5,681,569 | A | 10/1997 | Kuznicki et al. |
| 5,756,546 | A | 5/1998 | Pirotte et al. |
| 6,037,375 | A | 3/2000 | Sakamoto et al. |
| 6,235,095 | B1 | 5/2001 | Nohr et al. |
| 6,890,549 | B2 | 5/2005 | Artiss et al. |
| 7,105,195 | B2 | 9/2006 | Plank et al. |
| 7,115,586 | B2 | 10/2006 | Loftsson |
| 7,166,575 | B2 | 1/2007 | Quay |
| 7,202,233 | B2 | 4/2007 | Penkler |
| 7,423,027 | B2 | 9/2008 | Lai et al. |
| 7,547,459 | B2 | 6/2009 | Plank et al. |
| 2004/0076690 | A1* | 4/2004 | Ikemoto ............... A61K 31/075 424/729 |
| 2004/0137625 | A1 | 7/2004 | Wolff et al. |
| 2004/0161526 | A1 | 8/2004 | Schmid et al. |
| 2005/0266018 | A1 | 12/2005 | Boreyko et al. |
| 2007/0065396 | A1 | 3/2007 | Morariu |
| 2007/0116837 | A1 | 5/2007 | Prakash et al. |
| 2007/0270379 | A1 | 11/2007 | Freiss et al. |
| 2008/0069924 | A1 | 3/2008 | Zeller et al. |
| 2008/0154030 | A1 | 6/2008 | Chang et al. |
| 2008/0299166 | A1 | 12/2008 | Szente et al. |
| 2009/0012042 | A1 | 1/2009 | Ren et al. |
| 2009/0023682 | A1 | 1/2009 | Artiss et al. |
| 2009/0110746 | A1 | 4/2009 | Gainer |
| 2009/0227690 | A1 | 9/2009 | Strassburger et al. |
| 2009/0306343 | A1 | 12/2009 | Jungbauer et al. |
| 2010/0021533 | A1* | 1/2010 | Mazed ................... A61K 36/02 424/450 |
| 2010/0087392 | A1 | 4/2010 | Freiss et al. |
| 2010/0111854 | A1* | 5/2010 | Boyden ................ A61K 9/0019 424/1.49 |
| 2010/0323065 | A1* | 12/2010 | Smith ....................... A23L 2/02 426/72 |

FOREIGN PATENT DOCUMENTS

| | | |
|---|---|---|
| EP | 1167435 A2 | 1/2002 |
| FR | 2876914 A1 | 4/2006 |
| GB | 2067583 A | 7/1981 |
| JP | 60094912 A | 5/1985 |
| JP | 2001081102 A | 3/2001 |
| WO | 9909988 A1 | 3/1999 |
| WO | 0072331 A1 | 11/2000 |
| WO | 0250124 A1 | 6/2002 |
| WO | 03057135 A2 | 7/2003 |
| WO | 2006036159 A1 | 4/2006 |
| WO | 2006137959 A1 | 12/2006 |
| WO | 2007145663 A1 | 12/2007 |
| WO | 2008135674 A2 | 11/2008 |
| WO | 2008148080 A2 | 12/2008 |
| WO | 2012090018 A1 | 7/2012 |

OTHER PUBLICATIONS

IP Australia, "Patent Examination Report No. 1" in connection with related Australian Patent Application No. 2010366535, dated Mar. 27, 2015, 3 pages.

Brewster, Marcus E. et al., "Comparative interaction of 2-hydroxypropyl-β-cyclodextrin and sulfobutylether-β-cyclodextrin with itraconazole: Phase-solubility behavior and stabilization of supersaturated drug solutions", European Journal of Pharmaceutical Sciences, vol. 34, Feb. 26, 2008, pp. 94-103.

Cardenas, Claudette, Authorized Officer, European Patent Office, "International Preliminary Report on Patentability" in connection with related International Application No. PCT/IB2010/003503, dated May 29, 2013, 14 pages.

El-Maradny, Hoda A. et al., "Characterization of ternary complexes of meloxicam-HPβCD and PVP or L-arginine prepared by the spray-drying technique", Acta Pharmacologica Sinica, vol. 58, 2008, pp. 455-466.

Figueiras et al., "The Role of L-arginine in Inclusion Complexes of Omeprazole with Cyclodextrins," American Association of Pharmaceutical Scientists, vol. 11, No. 1, 2010, pp. 233-240.

Hubner, Werner, Authorized Officer, European Patent Office, "International Search Report" in connection with related International Application No. PCT/IB2010/003503, dated Oct. 21, 2011, 12 pages.

Hubner, Werner, Authorized Officer, European Patent Office, "Written Opinion of the International Searching Authority" in connection with related International Application No. PCT/IB2010/003503, dated Oct. 21, 2011, 15 pages.

Huet et al., Les β-cyclodextrines retardent la germination des embryons somatiques de carotte (Daucus carota L.), Comptes Rendus de L'Academie des Sciences Serie III Sciences de la Vie, vol. 314, No. III, 1992, pp. 171-177.

Kazuaki, Harata et al., Structure of β-Cyclodextrin Inclusion Complex with Nicotinamide, Chemical Pharmaceutical Bulletin, vol. 31, No. 4, 1983, pp. 1428-1430.

Japanese Patent Office, "Notice of Reasons for Rejection" in connection with related Japanese Patent Application No. 2013-546769, dated Apr. 25, 2014, 5 pages.

Müller et al., "Effect of Hydrotropic Substances on the Complexation of Sparingly Soluble Drugs with Cyclodextrin Derivatives and the Influence of Cyclodextrin Complexation on the Pharmacokinetics of the Drugs," Journal of Pharmaceutical Sciences, vol. 80, No. 6, 1991, pp. 599-604.

Pedersen, Morten, "Effect of Hydrotropic Substances on the Complexation of Clotrimazole with B-Cyclodextrin," Drug Development and Industrial Pharmacy, vol. 19, No. 4, 1993, pp. 439-448.

Salminen et al., "Action of Cyclodextrins on Germinating Seeds and on Micropropagated Plants," Starch, vol. 42, No. 9, 1990, pp. 350-353.

Suzuki et al., "Nutritional Significance of Cyclodextrins: Indigestibility and Hypolipemic Effect of α-Cyclodextrin," J. Nutr. Sci. Vitaminol, vol. 31, 1985, pp. 209-233.

Szejtli et al., "Erhöhung des Weizenernteertrages durch Behandlung des Saatgutes mit β-Cyclodextrin," Nahrung, vol. 25, No. 8, 1981, pp. 765-768.

Terekhova et al., "Study on complex formation of biologically active pyridine derivatives with cyclodextrins by capillary electrophoresis," Journal of Pharmaceutical and Biomedical Analysis, vol. 45, 2007, pp. 688-693.

Canadian Intellectual Property Office, "Examination Report" in connection with related Canadian Patent Application No. 2,822,995, dated Dec. 30, 2014, 5 pages.

New Zealand Intellectual Property Office, "First Examination Report" in connection with related New Zealand Patent Application No. 612459, dated Jan. 6, 2014, 2 pages.

(56) References Cited

OTHER PUBLICATIONS

New Zealand Intellectual Property Office, "First Examination Report" in connection with related New Zealand Patent Application No. 709165, dated Jul. 2, 2015, 3 pages.
Dokshina, N.J., Vice-head of the Department of Pharmacy of FIIP, Federal Agency for the Intellectual Property, "Office Action" in connection with related Russian Patent App. No. 2013133723, dated Jan. 26, 2015, 11 pgs.
European Patent Office, "Communication Pursuant to Article 94(3) EPC", in connection with related European Patent App. No. 10821423.0-1453, dated Sep. 8, 2017, 5 pgs.
Japanese Patent Office, "Decision of Rejection" in connection with related Japanese Patent App. No. 2014-226854, dated Dec. 5, 2016, 6 pgs.
New Zealand Intellectual Property Office, "First Examination Report" in connection with related New Zealand Patent App. No. 727462, dated Feb. 20, 2017, 3 pgs.
Australian Government / IP Australia, "Patent Examination Report No. 1", in connection with related Australian Patent App. No. 2016201846, dated Oct. 12, 2016, 2 pgs.
Canadian Intellectual Property Office, "Office Action" in connection with related Canadian Patent App. No. 2,822,995, dated Sep. 8, 2017, 4 pgs.

\* cited by examiner

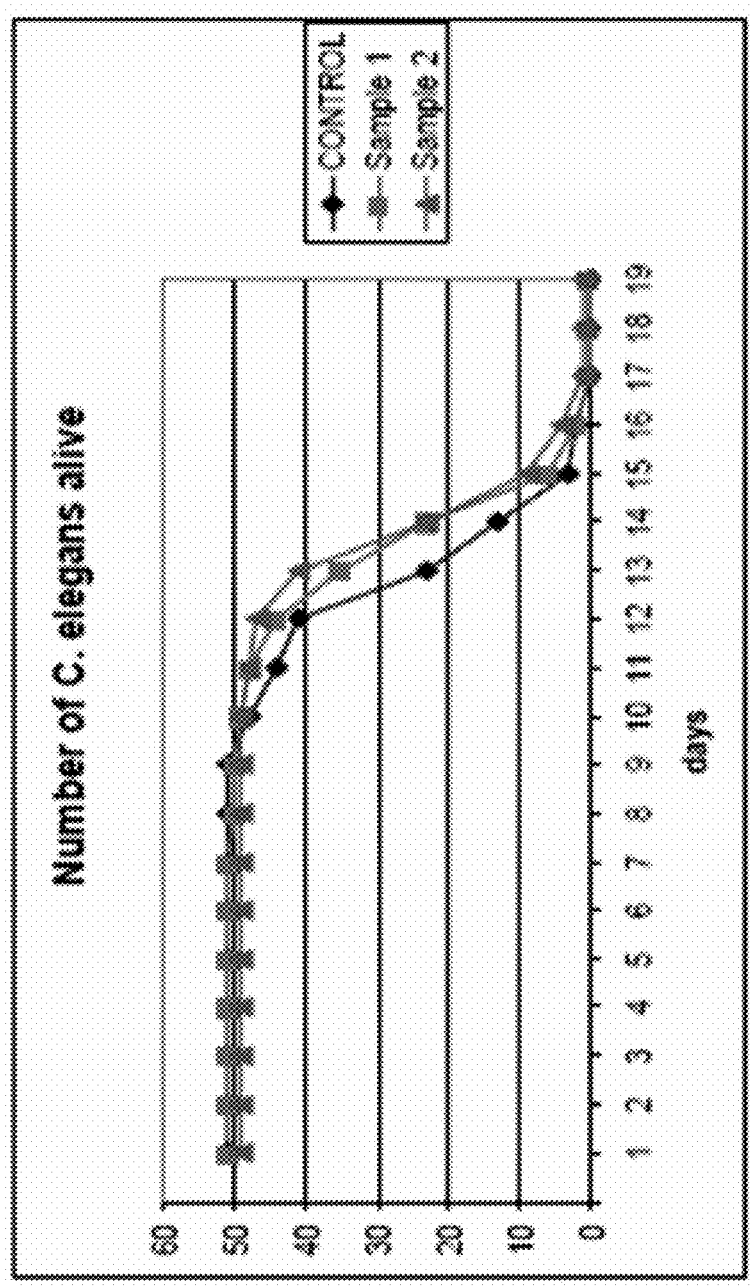

US 10,610,524 B2

CELLULAR HYDRATION COMPOSITIONS

CROSS-REFERENCE TO RELATED APPLICATIONS

This application is a continuation of U.S. patent application Ser. No. 12/983,234, filed Dec. 31, 2010, the disclosure of which is incorporated herein by reference.

FIELD OF THE INVENTION

The present invention generally relates to regulation of biological cell activity, particularly cell activity dependent on hydration state. More particularly, the present invention relates to a biologically active component that is constructed to increase an activity of a biological cell system by increasing the hydration of one or more components of that cell system. That biologically active component may include a primary carbohydrate clathrate subcomponent that increases the H-bonded structure of water. The present invention relates further to delivery of biological compounds in vivo for modifying mammalian physiological activity.

BACKGROUND OF THE INVENTION

Water molecules interact principally through hydrogen (H)-bonding and through alignment of dipole moments. For example, bonds between neighboring water molecules are reinforced, or stabilized, by alignment of bond axes with next-adjacent water molecules. In liquid state water, such alignments propagate into the surrounding aqueous medium and establish sub-micrometer scale molecular structure.

Examples of products and methods of using cyclodextrins as clathrates to form inclusions with bioactive guest molecules to improve solubility and/or bioavailability of pharmaceutical compounds are described in: U.S. Pat. Nos. 7,115,586 and 7,202,233, and U.S. Patent Application Publication Nos. 2004/0137625, and 2009/0227690, the complete disclosures of which are hereby incorporated by reference for all purposes.

Examples of products and methods of using products containing clathrates that bind hydrophobic biomolecules are described in U.S. Pat. Nos. 6,890,549, 7,105,195, 7,166,575, 7,423,027, and 7,547,459; U.S. Patent Application Publication Nos. 2004/0161526, 2007/0116837, 2008/0299166, and 2009/0023682; Japanese Patent Application JP 60-094912; Suzuki and Sato, "Nutritional significance of cyclodextrins: indigestibility and hypolipemic effect of α-cyclodextrin" J. Nutr. Sci. Vitaminol. (Tokyo 1985; 31:209-223); and Szejtl et al., Staerke/Starch, 27(11), 1975, pp. 368-376, the complete disclosures of which are hereby incorporated by reference for all purposes.

U.S. Patent Application Publication No. 2009/0110746 describes chemical agents which have the property of increasing aqueous diffusivity of dissolved molecular oxygen ($O_2$) in the human body, wherein cyclodextrins may be included as secondary "carrier" components to improve the solubility of primary pro-oxygenating agents, and wherein cyclodextrins are not contemplated as agents to directly alter aqueous diffusivity, tissue oxygenation, water structure, or cellular hydration.

BRIEF DESCRIPTION OF THE DRAWINGS

FIG. 18 shows population survival curves for nematodes living in media with and without a cyclodextrin inclusion complex as an active component of hydration according to the present disclosure.

DETAILED DESCRIPTION

Figure 1:
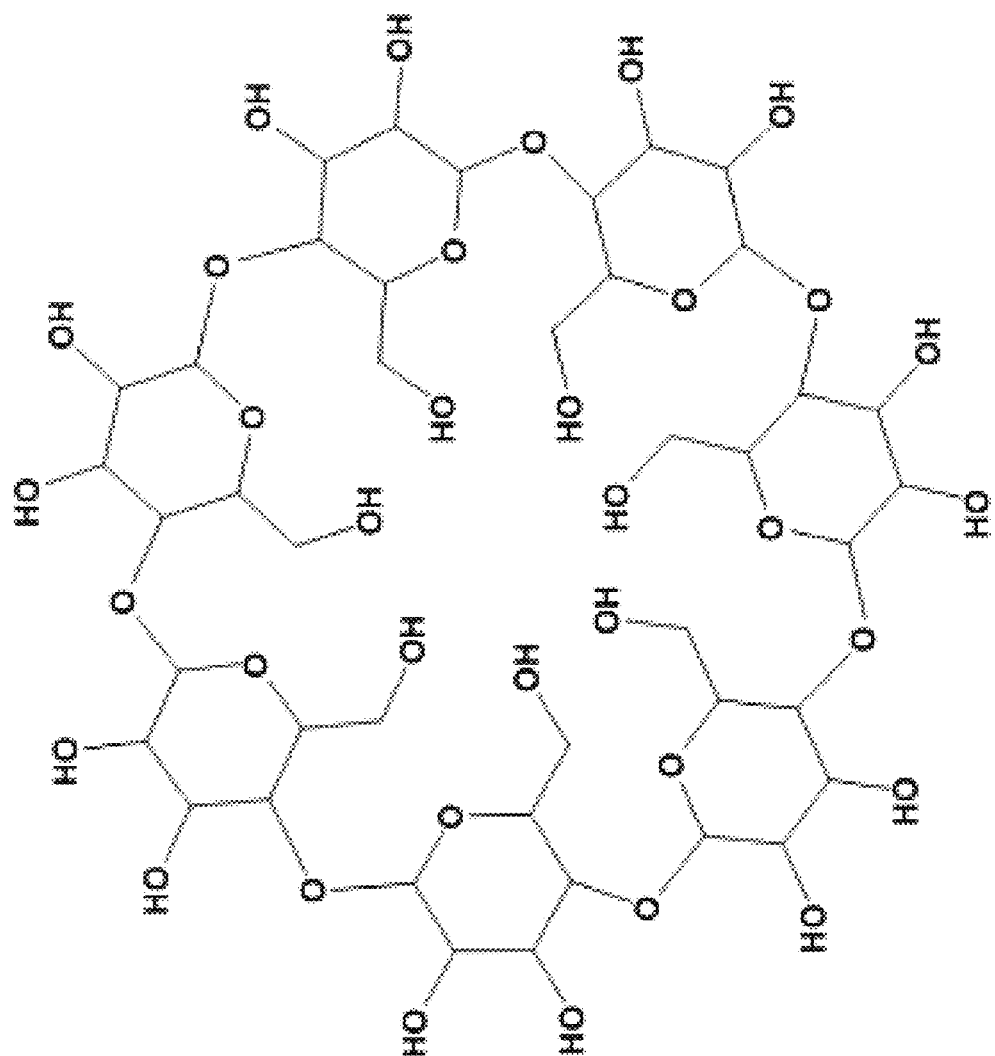
FIG. 1 shows a chemical bond model of β-cyclodextrin, a cyclic oligosaccharide having seven α[1-4] linked glucose units.

Water structure is purposefully increased, or organized, by addition of one or more solutes or suitable molecular aggregates whose surfaces are capable of strongly competing with water molecules for H-bonding and/or dipole orientation. In particular, factors and agents that strengthen water molecule interactions and increase water structure thereby alter the hydration, or solvation, of a further molecular surface. Thus, a primary solution additive that increases water structure may increase hydration interactions (e.g., bonding strength and kinetics) with a molecular surface of a secondary solution component, or alternatively decrease such interactions, depending on the H-bonding surface characteristics of the secondary component.

In addition, factors that modify water structure typically change the average distance between water molecules, and may thereby increase or decrease water density. For example, as water temperature decreases below its freezing point, H-bonding between the water molecules overcomes the kinetic energy of the water molecules, resulting in an increase in water structure that decreases the density of frozen water by approximately 9%. Similarly in liquid state water, an increase in the strength of water H-bonding increases the average distance between water molecules, which is observed as an increase in specific volume (i.e., decrease in density). A decrease in density of liquid water may increase the diffusivity of a dissolved solute. Thus, an aqueous additive component which decreases water density may increase the diffusivity of a co-dissolved solute.

Chaotropes, as used herein, are aqueous solute additives that disrupt hydrogen bonded networks in aqueous solutions, and thereby act to decrease water structure. Chaotropes typically are less polar and have weaker H-bonding potentials than water molecules. Chaotropes may preferentially bind to non-polar solutes and particles, and thereby increase solubility of a non-polar solute.

Kosmotropes, as used herein, are solutes that promote strong and extended H-bonded networks in aqueous solutions, and which thereby increase and/or stabilize the sub-micrometer scale structure of water molecule interactions. A kosmotrope having an H-bonding chemical potential greater than that of water, and/or having a dipole moment greater than that of water, may increase H-bonded networks between water molecules. Further, by strengthening hydration structure, a kosmotrope may increase hydration interactions at a molecular surface, which may include a binding site between molecules. A kosmotrope may thus be used as an aqueous solution additive to stabilize molecular interactions.

Further, a kosmotrope may increase the effective chemical activity of a dissolved co-solute. An increase in the strength of H-bonding interactions between water molecules causes water to adopt a more open architecture having a lower specific density and higher specific volume. Thus, by causing a decrease in density, addition of a kosmotrope to an aqueous solution may increase a diffusivity of one or more of a dissolved co-solute species or compound. Increasing the diffusivity of a solute species or compound may increase its reactivity, chemical potential, effective concentration, and availability.

As discussed herein, clathrate components are amphipathic carbohydrate compounds which have external surfaces that are hydrophilic and H-bond strongly with water, and also internal surfaces that are less hydrophilic. A clathrate's internal surface may selectively bind a molecular structure which is relatively non-polar or less hydrophilic than water.

An inclusion complex, as used herein, is a chemical complex formed between two or more compounds, where a first compound (also referred to as a host) has a structure that defines a partially enclosed space into which a molecule of a second compound (also referred to as a guest) fits and binds to the first compound. The host molecule may be referred to as a clathrate, and may bind the guest molecule reversibly or irreversibly.

A biological cell, as used herein, is the self-replicating functional metabolic unit of a living organism, which may live as a unicellular organism or as a sub-unit in a multicellular organism, and which comprises a lipid membrane structure containing a functional network of interacting biomolecules, such as proteins, nucleic acids, and saccharides. Biological cells include prokaryote cells, eukaryotic cells, and cells dissociated from a multicellular organism, which may include cultured cells previously derived from a multicellular organism.

A biological cell system, as used herein, is a functionally interconnected network of biological cells and/or sub-cellular elements, which may include living cells, non-living cells, cellular organelles, and/or biomolecules.

A bioactive molecule, as used herein, is a molecular compound having a functional activity in a biological cell system.

A biomolecule, as used herein, is a molecular compound that is synthesized by a biological cell. Biomolecules include compounds normally synthesized by cells, and compounds synthesized by genetically engineered cells, and chemically synthesized copies of cell-derived compounds.

A biomolecular surface, as used herein, is an outer atomic boundary of a biomolecule, which may include a biochemical interaction surface, such as a binding site.

Cellular components, as used herein, are functional elements of a biological cell, which include biomolecules, biomolecule complexes, organelles, polymeric structures, membranes and membrane-bound structures, and may further include functional pathways and/or networks, such as a sequence of molecular events.

The density of a substance is the mass per unit volume of that substance under specified conditions of temperature and pressure.

The specific volume of a substance is the volume per unit mass of the substance, which may be expressed, for example, as $m^3/kg$. The specific volume of a substance is equivalent to the reciprocal of the density of that substance.

A biologically active component, as used herein, is a molecular substance that modifies (increases or decreases) an activity of a biological cell system.

A bioactive agent, as used herein, is a substance that when added to a biological cell system, or to a cellular component, causes a change in the biological activity of that system, or that component.

The bonded structure of water, as used herein, refers to the network of H-bonds that hold and organize the orientation of water molecules in liquid and solid states. Water structure, as used herein, increases when H-bonds between water molecules at a given temperature are strengthened, and decreases when H-bonds between water molecules at a given temperature are weakened.

An interaction between cellular components, as used herein, refers to a chemical binding between biomolecular surfaces. Such interaction may include binding between two biomolecules, such as a ligand and its specific receptor. Alternatively, such interaction may include binding between a biomolecule and an organelle, such as a cell membrane.

Extracellular signals, as used herein, are biomolecules that can modify (increase or decrease) an activity of a cell when applied to the outside of the cell. An extracellular signal may bind to a component of the cell's plasma (outer) membrane, or alternatively may pass through the plasma membrane to regulate an intracellular activity. Extracellular signals may include, but are not limited to, extracellular matrix components; cell membrane components such as glycoproteins and glyocolipids; antigens; and diffusible biomolecules such as nitric oxide.

An intracellular messenger, as used herein, is an internal component of a biological cell that has an active state, and which serves in an active state as an intermediate signal to transmit an extracellular signal to an intracellular target.

A pharmacological agent, as used herein, is a synthetic chemical substance that binds to and thereby alters the activity of a biomolecule or a biomolecule complex.

The present invention includes active compositions that increase an activity of a biological cell system by increasing the hydration of one or more components of that cell system.

Preferably, an active composition for modifying cellular hydration includes a primary carbohydrate clathrate component that increases the H-bonded structure of water. In some examples, the active composition preferably includes a primary carbohydrate clathrate component that increases the H-bonded structure of water and a secondary solute compound, which may be a bioactive agent. In some examples, the active composition preferably includes an inclusion complex formed between a clathrate component and a complex-forming compound, which may be a bioactive agent.

Biological cells are multi-compartment structures, comprising chemically active water-based chambers and lipid-based membranes. The structure and activity of cells derives from highly selective chemical bonding associations between their biomolecular components, such as lipids, structural proteins, enzymatic proteins, carbohydrates, salts, nucleotides, and other metabolic and signaling biomolecules. The strength and specificity of biomolecule bonding reflects complementary chemical topologies at the bonding interface. Hydrophilic and/or hydrophobic surfaces commonly dominate the chemical topology of biomolecular bond interfaces. In aqueous systems, hydrophobic and hydrophilic interactions are substantially driven by competing hydration interactions with molecules of water, whose concentration exceeds 50 M.

Cellular hydration, as used herein, refers to interaction between water molecules and biomolecular components of a cellular system. Cellular hydration may be modified by changing the strength and/or kinetics of H-bonding between water molecules and biomolecular surfaces.

An aqueous solution additive that modifies water structure may, by modifying the hydration of biomolecular binding surfaces, alter the strength, kinetics, and/or specificity of binding between cellular components. For example, a kosmotrope aqueous additive that increases water structure may alter the strength, kinetics, and/or specificity of binding between a secreted intercellular signaling factor and a cognate receptor located in the plasma membrane of a potential target cell for that factor, and hence bias the outcome of a cellular signaling network.

Clathrates that are suitable as active components of cellular hydration according to the present invention include amyloses and cyclodextrins. Amyloses are linear polysaccharides of D-glucose units. As shown in FIG. 1, cyclodextrins are macrocyclic oligosaccharides of D-glucose units linked by $\alpha(1\text{-}4)$ interglucose bonds. Amylose and cyclodextrin are readily prepared in large quantities from hydrolyzed starch. Cyclodextrin preparation includes enzymatic conversion, most commonly using the enzyme cyclodextrin-glycosyl transferase produced by *Bacillus* strains.

Figure 2:
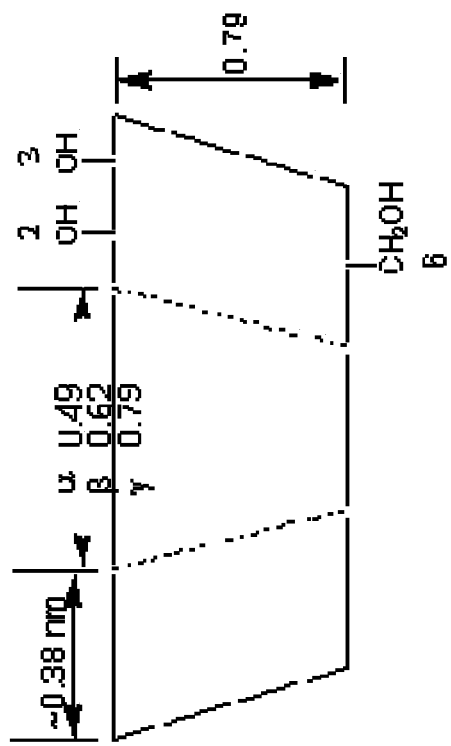
FIG. 2 shows a structural model of cyclodextrins having an overall toroid topology.
Figure 2:
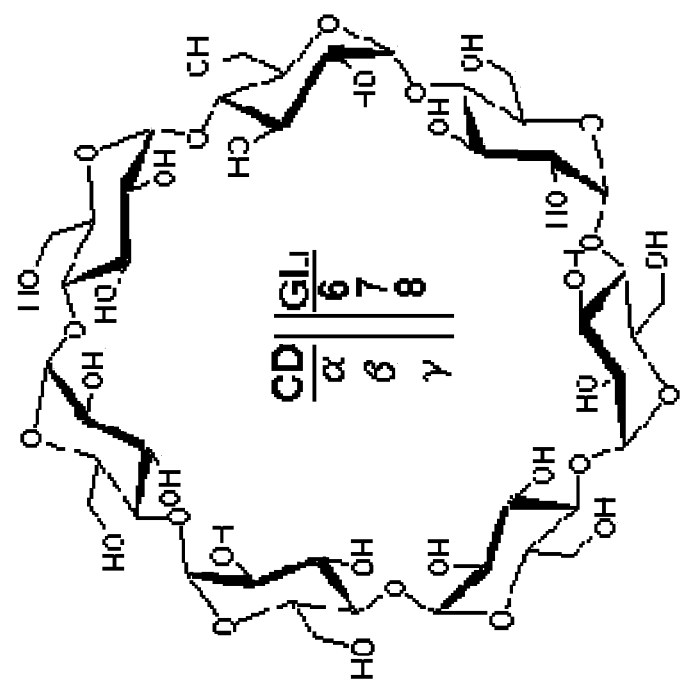

As shown in FIG. 2, cyclodextrins may differ by the number of glucose units included in the ring. Cyclodextrin species include $\alpha$-cyclodextrin (6 units), $\beta$-cyclodextrin (7 units), $\gamma$-cyclodextrin (8 units), and $\delta$-cyclodextrin (9 units). Parent cyclodextrins, as used herein, are natural, chemically underivatized $\alpha$-$\beta$- and $\gamma$-cyclodextrins, having 18 ($\alpha$-), 21 ($\beta$-) and 24 ($\gamma$-) free, unmodified hydroxyl groups, respectively.

Figure 3:
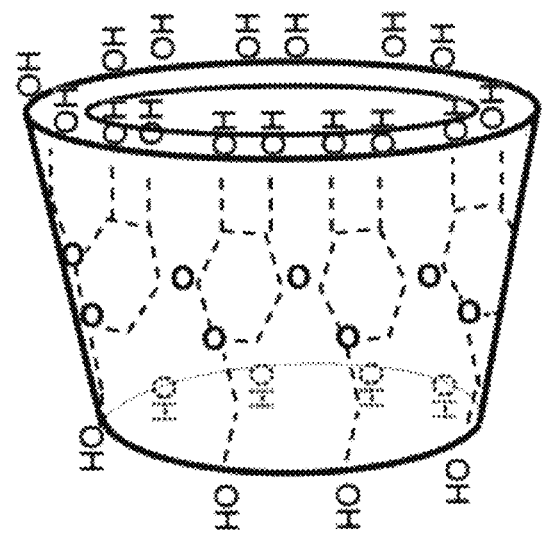
FIG. 3 shows a cyclodextrin structural model including the disposition of glucosyl hydroxyl groups along the toroid rims.

As schematically shown in FIG. 3, cyclodextrins have a toroid topology, a shape which generally resembles a truncated cone, or half of an open-ended barrel. Accordingly, a cyclodextrin may be described as including an exterior chemical surface, which includes the outer surface and the rims of the barrel, and an interior chemical surface surrounding an internal cavity (the inside of the barrel).

Cyclodextrin exterior surfaces include a high density of hydrophilic chemical groups that H-bond with water. In particular, the hydroxyl groups of the parent $\alpha$-cyclodextrin, $\beta$-cyclodextrin, and $\gamma$-cyclodextrin structures are all concentrated at the ends of the cyclodextrin barrel. More particularly, cyclodextrin hydroxyl (—OH) chemical groups are located along the barrel rims, and their orientation is sterically restricted. Hydroxyl groups at glucose position C(6), which may be called primary OH groups, point in a counter-clockwise direction with respect to the narrower open end of the cyclodextrin barrel. Hydroxyl groups at glucose position C(2), which may be called secondary hydroxyl groups, angle in a clockwise direction with respect to the wider open end of the cyclodextrin barrel.

The high density and constrained orientation of cyclodextrin hydroxyl groups creates particularly strong H-bonding surfaces at both ends of the cyclodextrin barrel. Physicochemical analysis and solvation modeling of cyclodextrins show water molecules adjacent the cyclodextrin have fixed positions and low angular (rotational) mobility. Usefully, species of cyclodextrin, which differ in barrel diameter as well as number of hydroxyl groups, also differ in the number and mobility of strongly bound water molecules.

Figure 4:
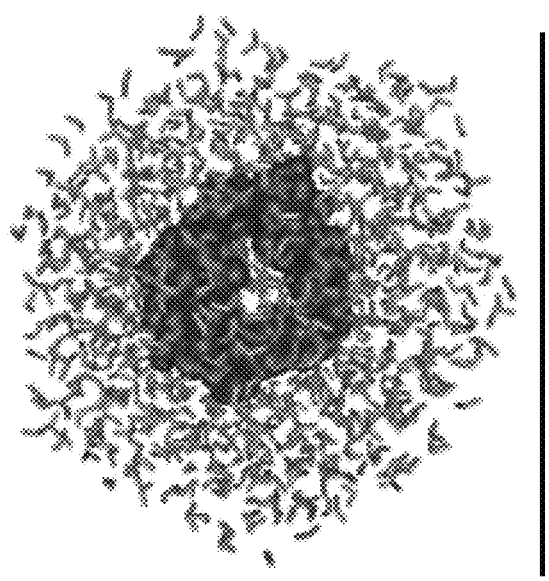
FIG. 4 depicts a calculated molecular dynamic distribution of water molecules surrounding a β-cyclodextrin molecule at 1 picosecond after initial contact.
Figure 5:
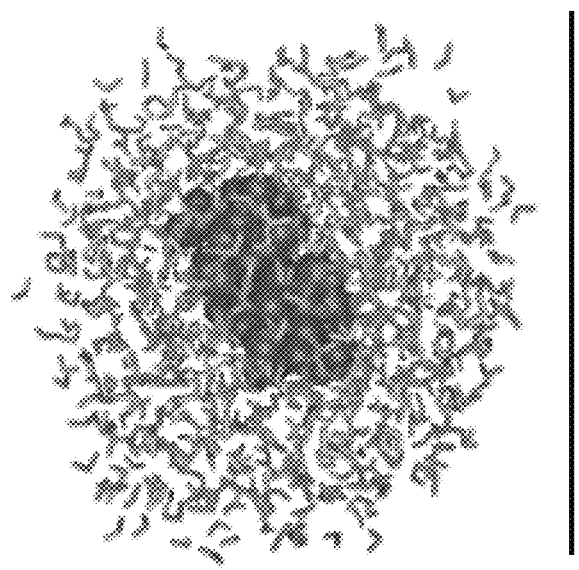
FIG. 5 depicts the calculated molecular dynamic distribution of water molecules of FIG. 4 at 1000 picoseconds after initial contact, including a more organized open water structure.

The H-bonding activity of a cyclodextrin compound may propagate into a surrounding aqueous medium. As shown in FIGS. 4 and 5, dynamic modeling of a cyclodextrin molecule introduced into a defined population of water molecules at standard temperature and pressure causes a nanosecond reorganization of water throughout the volume. FIG. 4 depicts a population distribution at one picosecond (ps) after initiating the mixing simulation; FIG. 5 depicts a redistribution of the same population at 1000 ps (1 nanosecond), wherein water molecules have adopted a more open structure.

In some examples, a cyclodextrin may function as an active component of cellular hydration through a kosmotrope activity that increases the bonded structure of water, wherein an increase in H-bonding between water molecules modifies the hydration of biomolecular surfaces, and thereby alters the strength, kinetics, and/or specificity of binding between cellular components.

In some examples, a cyclodextrin may function as an active component of cellular hydration through a kosmotrope activity that increases the bonded structure of water, wherein stronger H-bonding between water molecules causes an open water structure having a lower specific density (i.e., a higher specific volume), and wherein a rate of diffusion of bioactive molecules is increased. Such examples may include a soluble bioactive molecule such as an enzyme, enzyme substrate, nutrient, metabolite, cytokine, neurotransmitter, hormone, extracellular signal, intracellular messenger, or pharmacological agent.

An active component of cellular hydration that increases a rate of diffusion in water may regulate one of the many biological processes that are limited by the rate of change in the concentration of a bioactive component. For example, clearance of a neurotransmitter from synaptic clefts is commonly diffusion limited, including the passive dispersal of glutamate from excitatory synapses in the mammalian brain, and the active catabolism of acetylcholine at vertebrate neuromuscular synapses by the diffusion-limited enzyme acetylcholine esterase. Similarly, the activity of electrically excitable cells, such as muscle cells, is commonly coordinated by the diffusion-limited changes in the concentration of the intracellular second messenger signal calcium.

The cellular hydration activity of a cyclodextrin may be modified, either increased or decreased, by forming an inclusion complex with a complex-forming agent. Internal surfaces of cyclodextrins lack hydroxyl groups, are less hydrophilic than the surrounding aqueous environment, and thereby preferentially bind co-solute molecules having low hydrophilic and H-bonding potential.

Upon ingestion by an animal, carbohydrate clathrate compositions that increase the hydrogen bonding structure of interstitial and intracellular fluids may improve cellular hydration, including hydration structure at cell membrane surfaces as well as solvation of biomolecules that sub-serve healthy cell function. Improved cellular hydration may support healthy cell function by, for example, increasing the import, export, and/or diffusivity of solutes, nutrients, waste products, cytokines, metabolites, and other molecular agents supportive of cell function, differentiation, repair, growth, and survival, and by stabilizing cellular membranes in vulnerable tissues, such as muscle and nerve.

In some examples, a carbohydrate inclusion complex ingested by an animal may increase water H-bonding structure and thereby improve cellular hydration and/or diffusivity of cellular components. In some examples, a carbohydrate inclusion complex ingested by an animal may dissociate to release a free (i.e., non-complexed) cyclodextrin clathrate component that increases water hydrogen-bonding structure and thereby improves cellular hydration and/or diffusivity of cellular components. In some examples, a carbohydrate inclusion complex may increase water structure and improve cellular hydration without dissociating. In some examples, a carbohydrate inclusion complex may dissociate into a clathrate component for increasing water structure and cellular hydration, and a complex-forming agent which may further increase water-structure and/or provide other beneficial properties, such as nutrition or flavor.

The carbohydrate clathrate compositions of the present invention may be provided in various forms, including being formed into a solid powder, tablet, capsule, caplet, granule, pellet, wafer, powder, instant drink powder, effervescent powder, or effervescent tablet. Some carbohydrate clathrate compositions may also be formed as, or incorporated into, aqueous beverages or other food products. Such carbohydrate clathrate compositions may be inclusion complexes that remain reasonably stable during storage, so that the clathrate component does not dissociate from the complex-forming agent and form a stronger complex with another compound that reduces the kosmotropic activity of the complex and thereby decrease its ability to improve cellular hydration.

The present disclosure also provides methods for improving cellular hydration in an animal, such as a human. For example, some methods may include (a) preparing a beverage by dissolving an inclusion complex formed by a carbohydrate clathrate component and a complex-forming agent capable of dissociating from carbohydrate clathrate component under physiological conditions, and (b) having the animal orally ingest the beverage, whereupon the carbohydrate clathrate component dissociates from the complex-forming agent and modifies the strength, extent, and kinetics of the hydrogen bonded water structure at cellular biomolecular surfaces.

I. CARBOHYDRATE CLATHRATE COMPOSITION

The carbohydrate clathrate component may include any suitable carbohydrate including, but not limited to, α-cyclodextrin, β-cyclodextrin, γ-cyclodextrin, methylated β-cyclodextrins, 2-hydroxypropylated β-cyclodextrins, water soluble β-cyclodextrin polymers, partially acetylated α-, β-, and γ-cyclodextrins, ethylated α-, β-, and β-cyclodextrins, carboxy-alkylated β-cyclodextrins, quaternary-ammonium salts of α-, β-, and γ-cyclodextrins, an amylose (e.g., an acetylated amylose), and mixtures thereof.

In preferred embodiments, the carbohydrate clathrate may be selected based upon a kosmotrope activity that increases water structure alone or in combination with other solutes. Preferred cyclodextrin kosmotropes may include α-cyclodextrin, β-cyclodextrin, γ-cyclodextrin, 2-hydroxypropyl-cyclodextrins, carboxymethylated-cyclodextrins, and quaternary-ammonium-cyclodextrins.

Cyclodextrin derivatives may include alkylated, hydroxyalkylated, alkoxyalkylated, acetylated, quaternary ammonium salts, carboxyalkylated, maltosylated, and glucosylated derivatives. Alkyl groups of cyclodextrin derivatives may be straight chain or branched, may have main chain lengths of one to three carbons, and may have a total of one to six, and preferably one to three carbon atoms. Some non-limiting examples of cyclodextrin derivatives may include methylated beta-cyclodextrins, 2-hydroxypropylated β-cyclodextrins, water soluble beta-cyclodextrin polymers, partially acetylated α-, β-, and/or γ-cyclodextrins, ethylated α-, β-, and/or γ-cyclodextrins, carboxyalkylated β-cyclodextrins, quaternary ammonium salts of α-, β-, and/or γ-cyclodextrins, as well as mixtures of any combination of these derivatives, together or in combination with one or more cyclodextrins. An exemplary mixture of cyclodextrins may include a combination of α-, β-, and/or γ-cyclodextrin in a weight ratio range of about 1:1:1 to 2:2:1, respectively. The cyclodextrin may be in a hydrate crystalline and/or amorphous form, including but not limited to the hydrate and/or amorphous forms of α-, β-, and/or γ-cyclodextrin, and mixtures thereof.

If the carbohydrate clathrate composition is in solid form, the cyclodextrin component may be present in a concentration range of about 10-90% w/w, or about 15-70% w/w, or about 15-60% w/w. Preferably, the cyclodextrin component may be present in a concentration range of about 10-50% w/w, or about 15-40% w/w. More preferably, the cyclodextrin component may be present in a concentration range of about 20-25% w/w.

If the carbohydrate clathrate composition is in the form of an aqueous beverage, the cyclodextrin component may be present in a concentration range of about 0.01-75% w/v, or about 0.05-50% w/v, or about 0.1-25% w/v. Preferably, the cyclodextrin component may be present in a concentration range of about 0.1-10% w/v. More preferably, the cyclodextrin component may be present in a concentration range of 0.1-5% w/v.

The carbohydrate clathrate composition may preferably include a clathrate capable of forming an inclusion complex with a variety of complex-forming agents, such as amino acids, vitamins, flavorants, odorants, colorants, and the like. Non-exclusive examples of carbohydrate clathrate components capable of binding a complex-forming agent to form an inclusion may include α-cyclodextrin, β-cyclodextrin, β-cyclodextrin, 2-hydroxypropyl-cyclodextrins, caboxymethylated-cyclodextrins, quaternary-ammonium-cyclodextrins, amyloses, amylose derivatives, or any desired mixture of these.

A cyclodextrin clathrate component may be further selected based upon its desired binding properties with selected complex-forming agents. Non-limiting examples of acceptable cyclodextrins may include commercially available and government regulatory approved forms of α-, β- and γ-cyclodextrins. The number of glucose units determines the internal dimensions of the cavity and its volume, and may determine a selectivity in forming inclusion complexes with a guest molecule. Selected complex-forming agents, when bound to a host cyclodextrin or other host carbohydrate clathrate, may modify the physico-chemical properties of the complexed host to increase its kosmotropic activity.

If the clathrate component is in the form of an amylose component, the amylose component may contain glucose units expressed as degree of polymerization (DP) in the range of DP=10-900, and more preferably DP=20-200, and most preferably DP=30-80. Amylose derivatives may include, but are not limited to, acetylated amyloses. The amylose component preferably may have a structure that includes α1,4-linked D-glucopyranoses in a helical arrangement that defines a central cavity for binding hydrophobic molecules. For example, the A- and B-starch helix of V-amylose may include a parallel, left-handed double helix defining a central cavity. The helices of amylose inclusion complexes may be stabilized by the hydrophobic forces created by the host-guest interactions, intermolecular H-bonds between glucoses in adjacent amyloses, and intramolecular H-bonds formed by adjacent turns of the helix. See Hinrichs, W., et al., "An Amylose Antiparallel Double Helix at Atomic Resolution," *Science,* (1987), 238(4824): 205-208, the complete disclosure of which is hereby incorporated by reference for all purposes. An amylose clathrate component may be used to form an inclusion complex with a complex-forming agent having a low molecular weight, such as the non-limiting examples of flavorants, colorants, vitamins, amino acids, and/or amines.

If the composition containing an amylose clathrate component is in solid form, the amylose component preferably may be present in a concentration range of about 10-90% w/w, or about 15-70% w/w, or about 15-60% w/w. More preferably, the amylose component may be present in a concentration range of about 10-50% w/w, or about 15-40% w/w. Most preferably, the amylose component may be present in a concentration range of about 20-25% w/w. If the composition containing the amylose clathrate component is in the form of an aqueous beverage, the amylose component preferably may be present in a concentration range of about 0.1-75% w/v, or about 1-50% w/v, or about 1-25% w/v.

II. COMPLEX-FORMING AGENT

In some examples, the clathrate compositions disclosed herein may optionally contain a complex-forming agent, which may include one or more amino acids, vitamins, flavorants, odorants, and/or other nutritional components, as well as combinations or mixtures of these agents. The carbohydrate clathrate compositions may further include one or more carbonation forming components for use in forming beverage products.

The complex-forming agents may strongly complex with the clathrate component so as to increase a kosmotropic activity and thereby influence cellular hydration. Alternatively, these agents may weakly complex with the clathrate component so as to have the capability of dissociating therefrom in order to allow a free clathrate component to increase water structure.

Non-limiting examples of amino acids suitable for forming inclusion complexes with the carbohydrate clathrate compositions of the present disclosure may include aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, salts thereof, and mixtures thereof. Also included are N-alkyl $C_1$-$C_3$ and N-acylated $C_1$-$C_3$ derivatives of these amino acids, and mixtures of any of the amino acids or derivatives thereof. Preferred complex forming amino-acids that may be included with cyclodextrins to increase water structure and cellular hydration include L-arginine, L-lysine, N-methyl-lysine, and L-carnitine.

Non-limiting examples of vitamins may include nicotinamide (vitamin $B_3$), niacinamide, niacin, pyridoxal hydrochloride (vitamin $B_6$), ascorbic acid, edible ascorbyl esters, riboflavin, pyridoxine, thiamine, vitamin $B_9$, folic acid, folate, pteroyl-L-glutamic acid, pteroyl-L-glutamate, salts thereof, and mixtures thereof. Preferred vitamins included with cyclodextrins to increase water structure and cellular hydration may include nicotinamide and niacinamide.

Non-limiting examples of flavorants may include apple, apricot, banana, grape, blackcurrant, raspberry, peach, pear, pineapple, plum, orange, and vanilla flavorants. Examples of flavorant related compounds include butyl acetate, butyl isovalerate, allyl butyrate, amyl valerate, ethyl acetate, ethyl valerate, amyl acetate, maltol, isoamyl acetate, ethyl maltol, isomaltol, diacetyl, ethyl propionate, methyl anthranilate, methyl butyrate, pentyl butyrate, and pentyl pentanoate. A flavorant may be selected so that it weakly binds to a selected cyclodextrin component with a binding constant in the range of about 10 to 800 $M^{-1}$, preferably 30 to 150 $M^{-1}$, and more preferably 40 to 100 $M^{-1}$.

Non-limiting examples of other taste improving components may include polyol additives such as erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, and reduced glucose syrup.

Non-limiting examples of colorants may include those that are known to be more water soluble and less lipophilic. Examples of colorants with those properties are betalains, such as betacyanins and betaxanthins, including vulgaxanthin, miraxanthin, portulaxanthin and indicaxanthin; anthocyanidins, such as aurantinidin, cyanidin, delphinidin, europinidin, luteolinidin, pelargonidin, malvidin, peonidin, petunidin and rosinidin, as well as all corresponding anthocyanins (or glucosides) of these anthocyanidins; and turmeric type colorants including phenolic curcuminoids, such as curcumin, demethoxycurcumin and bisdemethoxycurcumin.

All of the above examples of amino acids, vitamins, flavorants and related compounds may be in appropriate salt or hydrate forms.

The complex-forming agent may be selected to form an inclusion complex with a selected clathrate component. The complex-forming agent may bind to the clathrate component as a guest molecule in the cavity of the clathrate molecule, and/or may form a so-called outer sphere complex, where the selected weak complex-forming agent binds to the clathrate molecule at a position at or around the rim(s) of the clathrate. For example, the selected weak complex-forming agent may be bound to a cyclodextrin molecule at or around the primary and/or secondary hydroxyl groups at the rims of the cyclodextrin torus. Some complex-forming agents that form an outer sphere complex with the selected cyclodextrin may reduce or prevent self-aggregation of dissolved, hydrated cyclodextrin molecules by masking intermolecular hydrogen bonds that form between two neighboring cyclodextrin molecules in water.

If the carbohydrate clathrate composition is in solid form, the complex-forming agent may be present in a concentration range of about 1-50% w/w. Preferably, the complex-forming agent may be present in a concentration range of about 1-40% w/w or about 1-25% w/w. More preferably, the complex-forming agent may be present in a concentration range of about 5-15% w/w.

If the carbohydrate clathrate composition is in the form of an aqueous beverage, the complex-forming agent may be present in a concentration range of about 0.1-25% w/v or about 1-20% w/v. Preferably, the complex-forming agent may be present in a concentration range of about 1-15% w/v or about 1-10% w/v or about 3-8% w/v. More preferably, the complex-forming agent may be present in a concentration range of about 5-8% w/v.

III. THE INCLUSION COMPLEX

As noted above, the inclusion complex may include a clathrate host molecule complexed with one or more complex-forming agents. In the form of a solid product, such as a solid powder or tablet, the inclusion complex may exhibit some unique properties as compared to a solid composition containing essentially the same components, but without the preliminary formation of the inclusion complex. The inclusion complex is essentially a chemical entity having non-covalent hydrogen bonds formed between the clathrate molecule and the weak complex-forming agent molecule. The inclusion complex, in its solid form, has the potential of dissociating into the clathrate component for increasing water structure and the complex-forming agent, which may further increase water structure or provide other beneficial properties, such as nutrition or flavor, when the inclusion complex is introduced to an aqueous environment, such as upon dissolution in an aqueous beverage, or upon ingestion.

When in the form of a solid product, the clathrate component and one or more types of a complex-forming agent may be substantially in the form of an inclusion complex, as described above. Preferably, over about 25% of the clathrate component is complexed with one or more types of a complex-forming agent in the form of an inclusion complex. It is progressively more preferable to have over 35%, 45%, 50%, 60%, 70%, 80%, 90%, and 95% of the clathrate component complexed.

IV. CARBONATION-FORMING COMPONENTS

Some clathrate compositions may include carbonation-forming components that produce carbonation, or effervescence, upon dissolution into an aqueous environment. Carbonation-forming components advantageously may inhibit self-aggregation of clathrate molecules, thereby increasing clathrate surface area for structuring water and increasing cellular hydration.

Non-limiting examples of carbonation-forming components may include sodium carbonate, sodium bicarbonate, potassium carbonate and potassium bicarbonate. Preferred carbonation-forming components may include sodium carbonate, and sodium bicarbonate.

If the carbohydrate clathrate composition is in solid form, the carbonation-forming component may be present in a concentration range of about 1-60% w/w or about 5-60% w/w. Preferably, the carbonation-forming component may be present in a concentration range of about 5-45% w/w or 10-45% w/w. More preferably, the carbonation-forming component may be present in a concentration range of about 10-15% w/w.

If the carbohydrate clathrate composition is in the form of an aqueous beverage, the carbonation-forming component may be present in a concentration range of about 1-30% w/v or about 1-25% w/v. Preferably, the carbonation-forming component may be present in a concentration range of about 2-15% w/v or 2-10% w/v. More preferably, the carbonation-forming component may be present in a concentration range of about 2-5% w/v.

V. OTHER COMPONENTS

Some compositions may include yet other components that affect the taste and/or nutritional value of the composition. These additional components may include, but are not limited to, one or more of the following: flavor additives, nutritional ingredients and/or various hydroxyl-acids that act as clathrate aggregation-preventing additives in the formulations. Non-limiting examples of such other components may include citric acid, ascorbic acid, sodium chloride, potassium chloride, sodium sulfate, potassium citrate, europium chloride ($EuCl_3$), gadolinium chloride ($GdCl_3$), terbium chloride ($TbCl_3$), magnesium sulfate, alum, magnesium chloride, maltodextrin, mono-, di-, tri-basic sodium or potassium salts of phosphoric acid (e.g., inorganic phosphates), salts of hydrochloric acid (e.g., inorganic chlorides), sodium bisulfate. Non-limiting examples of hydroxyl-acids that prevent cyclodextrin aggregation may include isocitric acid, citric acid, tartaric acid, malic acid, threonic acid, salts thereof and mixtures thereof. These hydroxyl-acids also may exhibit some nutritional benefits. Other non-limiting examples of additional optional components, such as taste additives, that may be used include suitable organic salts, such as choline chloride, alginic acid sodium salt (sodium alginate), glucoheptonic acid sodium salt, gluconic acid sodium salt (sodium gluconate), gluconic acid potassium salt (potassium gluconate), guanidine HCl, glucosamine HCl, amiloride HCl, monosodium glutamate (MSG), adenosine monophosphate salt, magnesium gluconate, potassium tartrate (monohydrate), and sodium tartrate (dihydrate).

Preferred other components may include, for example, citric acid, ascorbic acid, and maltodextrin.

If the carbohydrate clathrate composition is in solid form, the one or more other components each may be present in a concentration range of about 1-30% w/w or about 1-25% w/w. Preferably, the one or more other components each may be present in a concentration range of about 1-20% w/w or 1-15% w/w. More preferably, the one or more other components each may be present in a concentration range of about 2-5% w/w.

If the carbohydrate clathrate composition is in the form of an aqueous beverage, the one or more other components may be present in a concentration range of about 1-20% w/v or about 1-15% w/v. Preferably, the one or more other components may be present in a concentration range of about 1-10% w/v or 1-5% w/v. More preferably, the one or more other components may be present in a concentration range of about 1-3% w/v.

VI. COMPONENT RATIOS

In addition to the above descriptions regarding the types and amounts of the various components that may be employed in the carbohydrate clathrate compositions disclosed herein, it is additionally noted that the relative amounts of these components can be described as well. Preferably, the weight ratio of the clathrate component to the complex-forming agent may be in the range of about 5:1 to 1:10, more preferably may be in the range of about 2:1 to 1:5, still more preferably may be in the range of about 2:1 to 1:2, and yet more preferably may be in the range of about 1:1 to 1:2.

Regarding the other possible components, such as flavor components, carbonation-forming components, and other components described above, the weight ratio of the clathrate component to each of the other components separately may be in the range of about 25:1 to 1:25, or about 10:1 to 1:10, or about 5:1 to 1:5, or optionally about 2:1 to 1:2, as well as 1:1.

VII. PREFERRED EMBODIMENTS

Preferred embodiments of the carbohydrate clathrate composition disclosed herein are provided as illustrations, and are not intended to limit the scope of this disclosure in any way.

Example 1

Effect of Cyclodextrin on Molecular Dynamics of Water Structure

A simulated water solvated cyclodextrin molecular system was created using HyperChem® 5.11 software (from HyperCube Inc, Gainesville, Fla.), with input parameters derived from single crystal analysis of cyclohepta-amylose dodecahydrate clathrate (or, β-cyclodextrin) reported by Lindner and Saenger (see: Carbohydr. Res., 99:103, 1982), and using a water periodic solvent box (3.1×3.1×3.1 nm$^3$) containing altogether 984 water molecules. Molecule conversion and atom type were adjusted to the proper format using TinkerFFE 4.2 (TINKER Software Tools for Molecular Design, Version 5.0, Jay William Ponder, Washington University, St. Louis, Mo.). Molecular mechanics and dynamics calculations were performed with Tinker 5.0 software after preliminary optimization of the truncated Newton-Raphson method using a Linux x86-64 operating system (Slamd 64 v12.2).

Molecular dynamics simulations were run using MM3 Force Field molecular mechanics software, at constant temperature (298 K) for 120 picosecond (psec), with 0.1 femtosecond (fsec) steps. Recordings were generated by dumping intermediate structures every 100,000 steps (equivalent to 10 psec elapsed time).

Observations:

At time zero of each simulation, the standard water solvent box contained one β-cyclodextrin clathrate molecule and a uniformly distributed population of 984 water molecules. FIGS. 4 and 5 show a representation of the central portion of the solvent box at particular elapsed times during one representative simulation. It will be appreciated that water molecule positions and orientations are represented as (bent) rods, while β-cyclodextrin is represented as a van der Waals surface. It will be further appreciated that FIGS. 4 and 5 depict a volume of the solvent box, and therefore compress a three dimensional molecular distribution into two dimensions.

FIG. 4 shows a central portion of the solvent box at 1 psec of elapsed time of a simulation. In particular, at 1 psec of elapsed time, water molecules immediately adjacent to β-cyclodextrin have acquired relatively static (stable) positions through H-bonding to cyclodextrin. Such water molecules may be referred to as a first hydration layer. However, the distribution of most water molecules in the solvent box remains generally similar to the starting distribution (1 psec previous), which is unstructured.

FIG. 5 shows the simulation of after 1000 psec (i.e., 1 nsec) of elapsed time. At 1000 psec, water molecules immediately adjacent to β-cyclodextrin continue to occupy relatively static (stable) positions. However, compared to 1 psec (FIG. 4), water molecules beyond the first hydration layer have acquired a more open microstructure.

Figure 6:
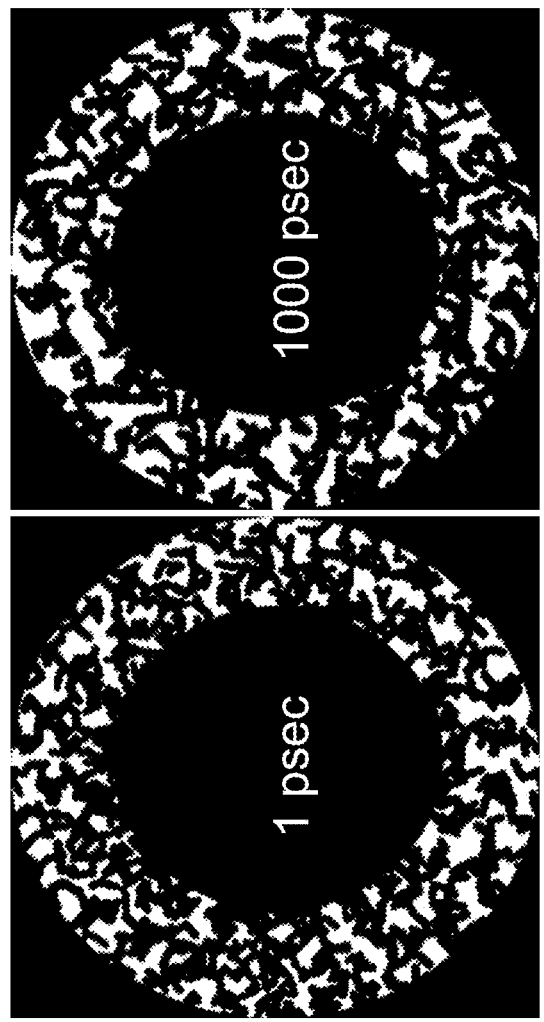
FIG. 6 shows thresholded images of the water molecule distributions shown in FIGS. 4 and 5.

Differences in water structure may be more readily observed in the absence of the perspective shadowing detail included in FIGS. 4 and 5. FIG. 6 shows alternative views of the water molecule distributions shown in FIG. 4 (left side, labeled 1 psec) and FIG. 5 (right side, labeled 1000 psec), which were produced by the following methods: image files for FIGS. 4 and 5, having 256 grey levels (8 bits), were opened in Photoshop 9.0 (Adobe, Inc), adjusted to 300 dpi, thresholded at grey level 207; images were cropped to an identical outer annulus diameter using the circle select tool, and the outer square corners filled with black (grey level 0), and then further cropped to blacken an inner annulus that barely includes the cyclodextrin molecule. The dimensions of the outer and inner annuli are identically applied to the compared images. The resulting thresholded representations qualitatively show water molecules surrounding the central (occluded) cyclodextrin molecule have a more open and coordinated structure at 1000 psec (e.g., right side panel of FIG. 6).

To quantitatively assess the change in microstructure of water represented in FIGS. 4-6, molecular density was approximated by measuring open paths through the depicted volume, a method similar to a mean free path analysis, where a mean free path in a defined volume of a molecular substance is inversely related to the density of the molecules. In particular, an open path between water molecules is shown by a white pixel element, and the number of open paths in the volume is readily quantitated using the histogram tool of Photoshop 9.0 to count the number of white pixel elements. Applied to the panels of FIG. 6, a measured increase of 2% was calculated for open paths at 1000 psec of elapsed time compared to open paths at 1 psec of elapsed time. For comparison, freezing of pure water results in a 9% decrease in density. As path length is inversely proportional to molecule density, the analysis indicates that dissolved cyclodextrins decrease the density of an aqueous solution by increasing the organization of water molecules.

In summary, the results indicate a rapid (psec) H-bonding adhesion between the outer surface hydroxyls of β-cyclodextrin and water molecules is followed by a slower (nanosecond) propagation of water molecule reorientation throughout the solvent box, resulting in a more open water structure. The measured results further indicate that a cyclodextrin may sufficiently increase H-bonding between water molecules in the surrounding aqueous volume to result in a decrease in the density of water.

Example 2

Effect of Cycodextrin Additives on Water Bonding Detected by IR Spectroscopy

Physical micro-structure studies of water, water-sugar interactions, and detection of sugar effects on increasing and decreasing water structure have preferentially employed infrared (IR) spectroscopy, and particularly near infrared (NIR) spectroscopy, as for example reported by Segtan et al. (see: Anal. Chem. 2001; 73, 3153-3161), and R. Giangiacomo (see: Food Chemistry, 2006, 96.3. 371-379.)

Hydration bond energies in pure waters and solutions of the same waters containing cyclodextrin compounds were assayed using IR spectroscopy in the near and middle infrared ranges. To record linear signals throughout an entire wavelength range, attenuation from water absorbance was minimized with a short optical length cuvette.

NIR range spectra were registered on a FOSS NIR Systems, Inc. 6500 spectrometer and Sample Transport Module (STM) using a 1 mm-es cuvette. Transmission spectra were collected from 1100-2498 nm using a lead sulfide (PbS) detector and Vision 2.51 software (2001; FOSS NIRSystems, Inc.)

A Perkin-Elmer Spectrum 400 FT-NIR/FT-IR spectrometer and UATR (Universal Attenuated Total Reflectance; ZnSe-diamond crystal, 1× flat top plate) sample handling unit were used to obtain spectra across 2500-15385 nm (reported as 4000-650 $cm^{-1}$). Measurements were performed at 24 C using a triglycine-sulfate (TGS) detector and Spectrum ES 6.3.2 software (PerkinElmer, 2008).

Three samples of water were used in the present study. A first water sample (USA I) was obtained from the U.S. and was purified by reverse osmosis, carbon filtration, ultraviolet light exposure, membrane filtration to 0.2 micron absolute, and ozonation. A second water sample (USA II) was also obtained from the U.S. A third water sample (BP I) was obtained from Budapest, Hungary. Capillary electrophroresis revealed similar ionic components differed in concentration between the three waters.

The following cyclodextrins were added to the above described water samples at a concentration range of 0.1%-5% w/v:

α-cyclodextrin (αCD also denoted as ACD), Lot. No. CYL-2322.
β-cyclodextrin (βCD also denoted as BCD). Lot. No. CYL-2518/2.
γ-cyclodextrin (γCD also denoted as GCD), Lot. No. CYL-2323.
2-hydroxypropyl-β-cyclodextrin (HPβCD, HPBCD), DS*=3.5, Lot. No. CYL-2232.
2-hydroxypropyl-γ-cyclodextrin (HPCD, HPGCD), DS*=4.8, Lot. No. CYL-2258.
carboxymethyl-β-cyclodextrin (CMBCD), Lot. No. CYL-2576.
quaternary-ammonium-β-cyclodextrin (QABCD).

For some examples, various inclusion complexes were formed between cyclodextrins and complex-forming bioactive agents, including the amino acids L-arginine and L-carnitine and the vitamin niacinamide (also known as nicotinamide). All reagents were of analytical purity. For some examples, L-arginine and nicotinamide were added in free form and alternatively in a cyclodextrin-complexed (molecularly entrapped) form to assess independent and co-dependent activities of a cyclodexrin and a bioactive agent. Concentrations of above additives in free form, and as cyclodextrin inclusion complex forms, were in the range of 0.1% to 5.0% w/v.

Figure 7:
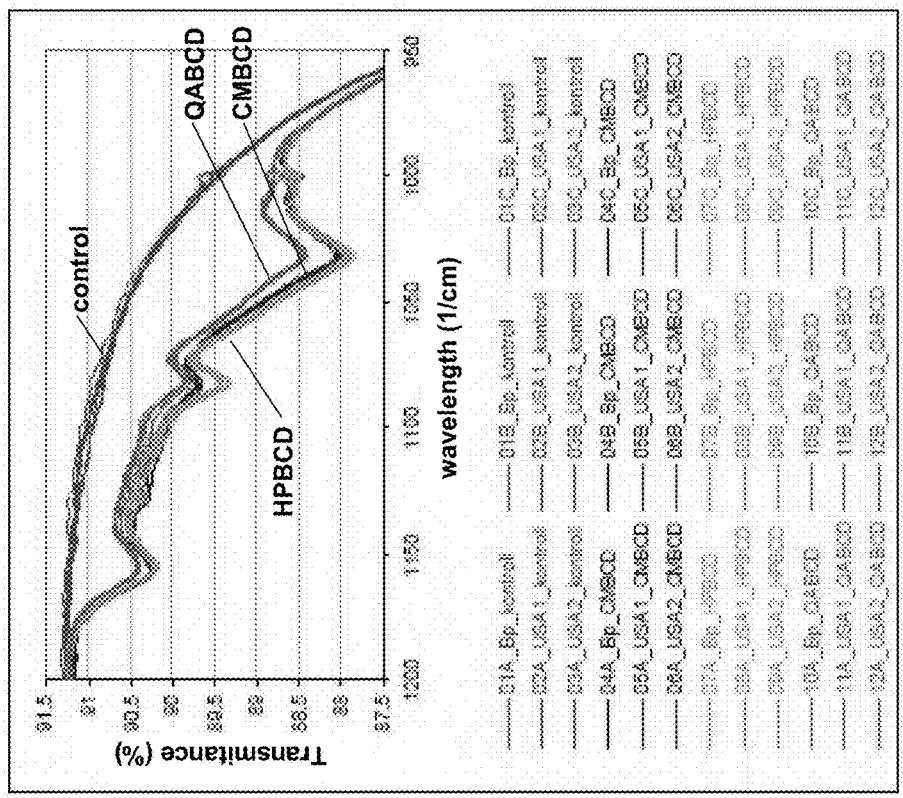
FIGS. 7-10 show a comparison of NIR spectra derivatives, including particular wavelength regions, for water samples with and without dissolved cyclodextrins.

Observations:

FIG. 7 shows second-derivative NIR spectra for the wavelength region 900-1200 nm. The results show water-bond interactions are significantly modified by addition of QABCD, and further significantly modified by addition of CMBCD and HPBCD.

Figure 8:
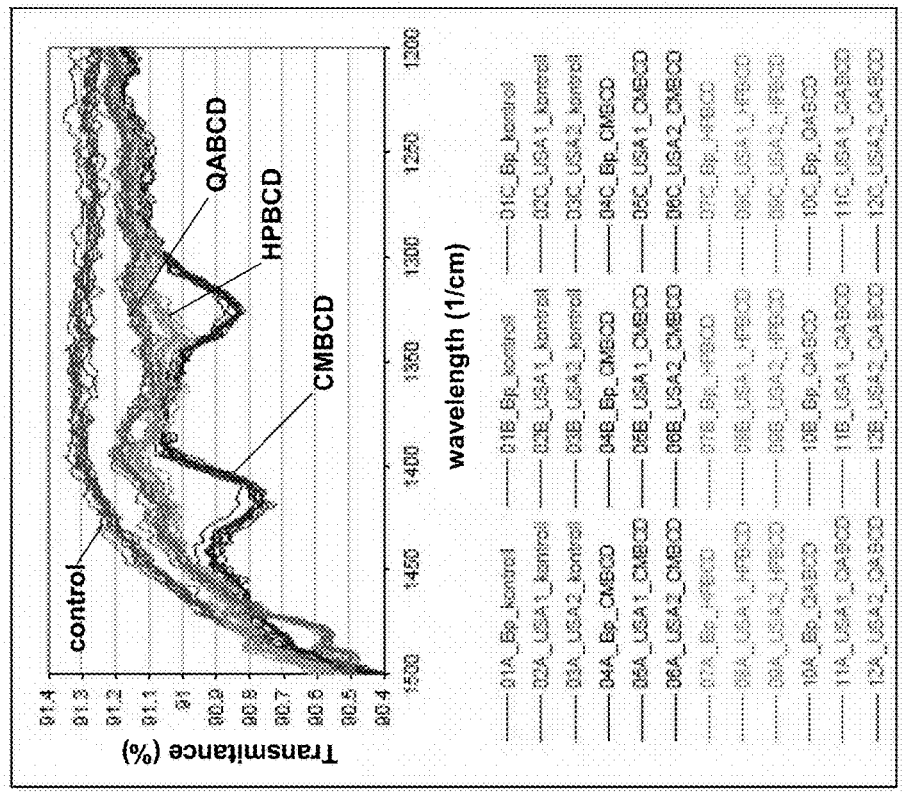

FIG. 8 shows second-derivative NIR spectra shown for 1200-1500 nm. The results show water-bond interactions are significantly modified by addition of QABCD and HPBCD, and further significantly modified by addition of CMBCD.

Figure 9:
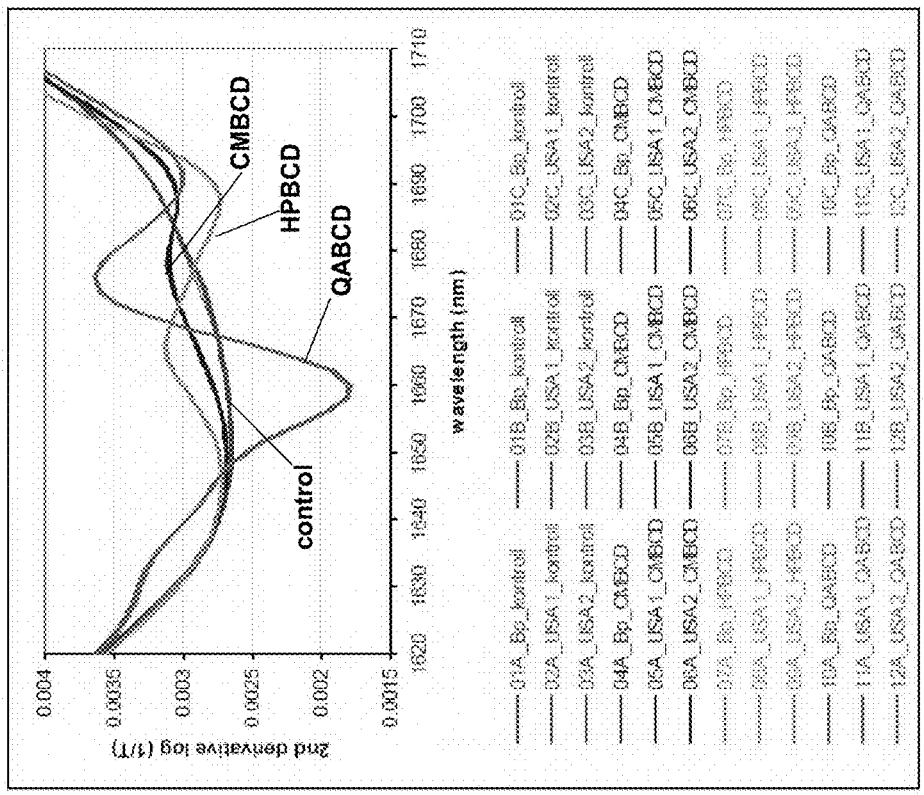

FIG. 9 shows second-derivative NIR spectra shown for 1620-1710 nm. The results show water-bond interactions are significantly modified by addition of CMBCD, QABCD, and HPBCD.

Figure 10:
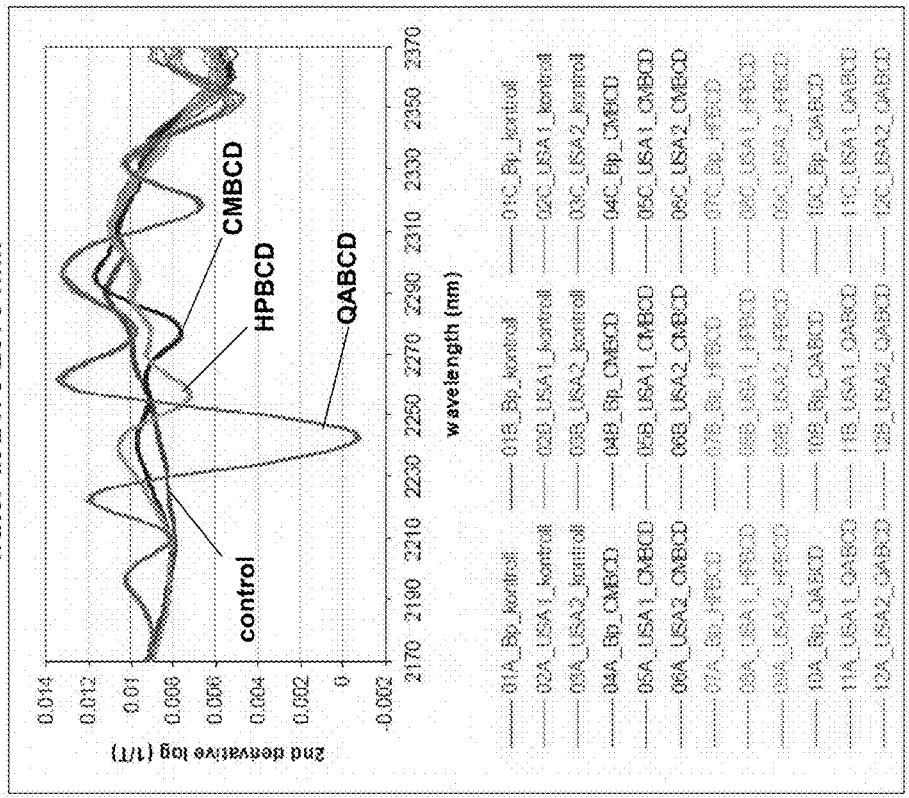

FIG. 10 shows second-derivative NIR spectra shown for 2170-2370 nm. The results show water-bond interactions are significantly modified by addition of CMBCD and HPBCD, and further significantly modified by addition of QABCD.

As shown in FIGS. 7-10, addition of cyclodextrins alters molecular bonding interactions of the aqueous medium. Referring particularly to FIG. 9, refined NIR spectra derivatives in the wavelength range of 1620-1770 nm show the carbon hydrogen bond related alterations involve CH3- CH2- and CH— groups of cyclodextrin additives. The significant spectral changes occurring in each cyclodextrin-treated water sample indicate the modified micro-structure of hydrogen bonds governed cluster systems in bulk water. This effect was largest in the water samples treated with charged quaternary-ammonium-β-cyclodextrins (QABCD), as shown for example in FIGS. 9 and 10.

Example 3

Acceleration of Plant Embryo Germination

Wheat seeds (*Triticum aestivum*) were germinated using USA I, USA II, and BP I waters described for Example 2. Germination rate using un-supplemented (control) water was compared to that with the same water variously supplemented with a cyclodextrin component, and/or a bioactive agent, as an active component of cellular hydration. For each condition, ten seeds were placed in continuous water contact in a Petri-type dish kept at 25 C in 12 hr light/dark cycles. Photometric images were recorded on days 1 to 6 after seeding. The percentage of seeds germinated was calculated and compared as a function of time and of the applied additive concentrations.

Water samples for seed germination were used alone with no additive, or containing cyclodextrins, or containing clathrate inclusion complexes of cyclodextrin with L-arginine or with nicotinamide (both obtained from Sigma Chemical Co.; St. Louis, Mo.), or with L-carnitine (from Lonza AG; Switzerland). Additives were included at 0.1 and 5. % (w/v). Additive solutions were prepared fresh on the day of germination start.

Parent cyclodextrins α-cyclodextrin (ACD), β-cyclodextrin (BCD), and γ-cyclodextrin (GCD), were obtained from Wacker Chemie (Munich, Germany). The following derivatized cyclodextrins were obtained from Cyclolab Ltd. (Budapest, Hungary): hydroxypropylated-beta-cyclodextrin (DS~3)(HPBCD), carboxymethylated-β-cyclodextrin (DS~3.5)(CMBCD), 2-hydroxy-3-N,N,N-trimethylamino) propyl-β-cyclodextrin chloride (DS~3.6)(QABCD).

Observations

Germination kinetics in control and additive-modified water under identical conditions were quantified as the percentage of the seeds having a sprout. Each determination consisted of 100 seeds for each parameter. Results are reported in Table 1, below, and in FIGS. 11-13.

A) Cyclodextrin/L-Arg Inclusion Complex Increases Seed Germination.

TABLE 1

Effect of α-cyclodextrin and L-arginine on wheat seed germination rate (values = percentage of total seeds)

| Days | control (water) | α-Cyclodextrin, 0.5% | L-Arg, 0.5% | α-CD/L-Arg inc. complex |
|---|---|---|---|---|
| 0 | 0 | 0 | 0 | 0 |
| 1 | 8 | 0 | 0 | 15 |
| 2 | 44 | 48 | 30 | 73 |
| 3 | 60 | 70 | 45 | 94 |
| 4 | 90 | 85 | 60 | 97 |

Figure 11:
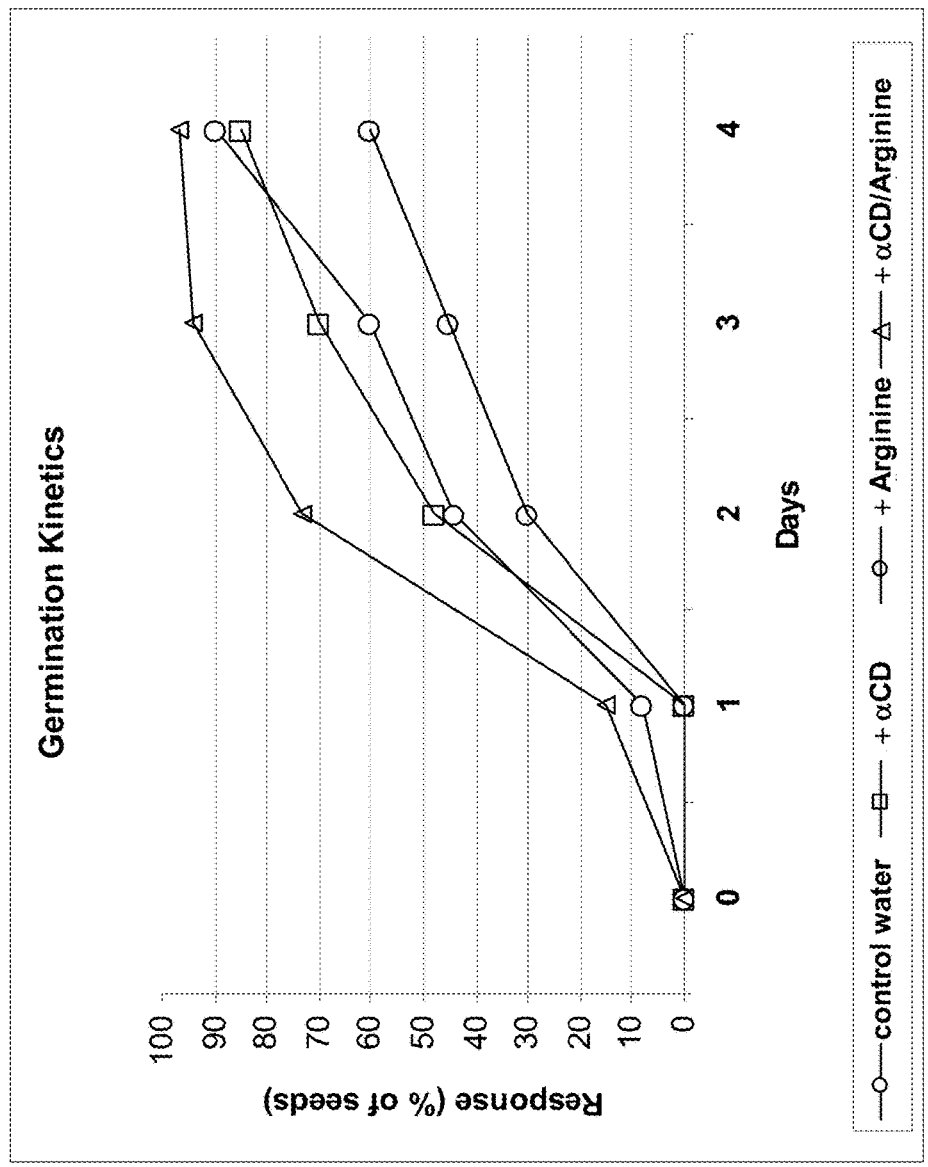
FIG. 11 shows a comparison of seed germination kinetics in water variably including a cyclodextrin, an amino acid, and a cyclodextrin/amino acid inclusion complex.
Figure 13:
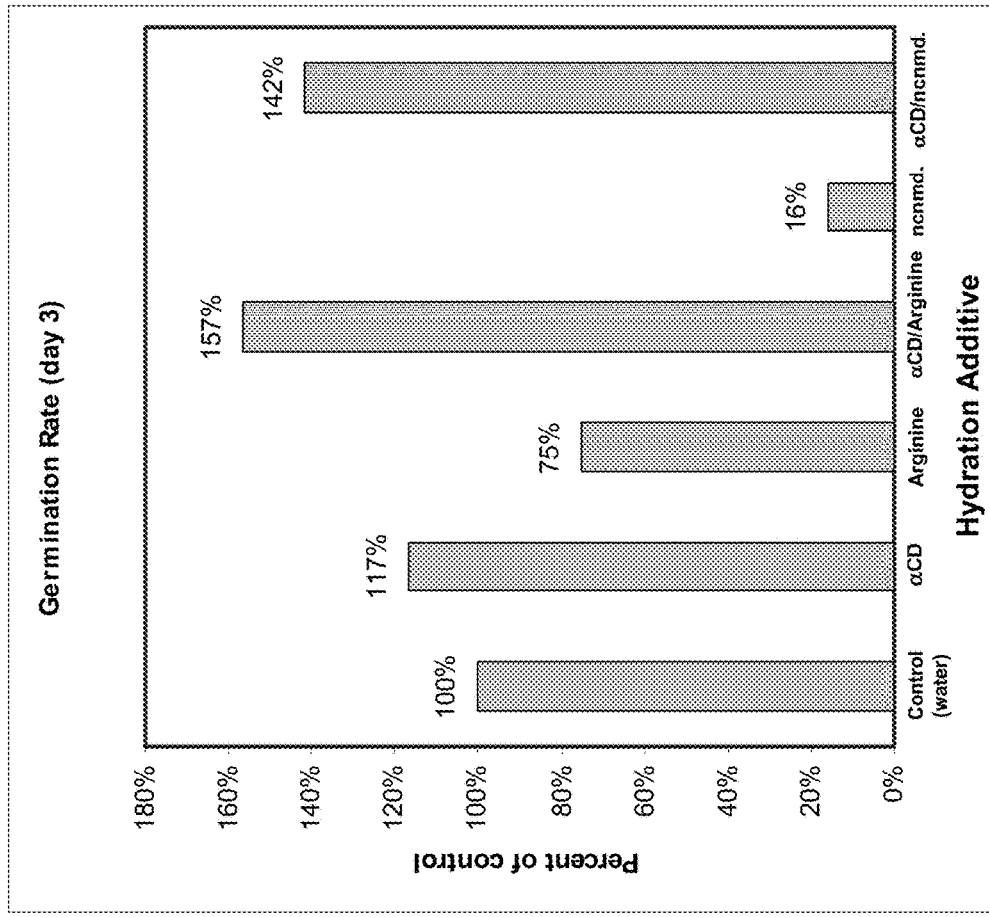
FIG. 13 shows a comparison of seed germination rate in water variably including active components of hydration according to the present disclosure.
Figure 14:
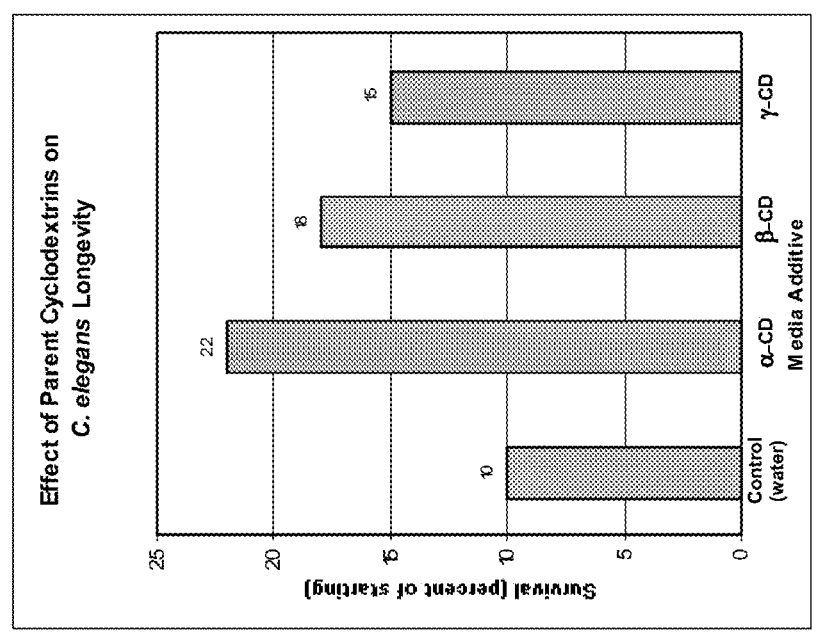
FIG. 14 shows a comparison of nematode longevity in media variably including cyclodextrins as an active component of hydration according to the present disclosure.
Figure 15:
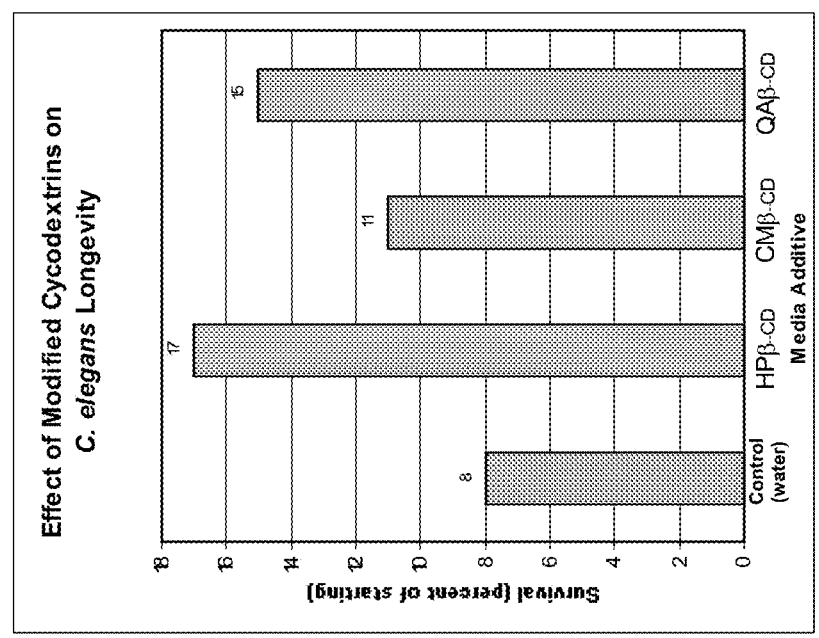
FIG. 15 shows a comparison of nematode longevity in media variably including derivatized cyclodextrins as an active component of hydration according to the present disclosure.
Figure 16:
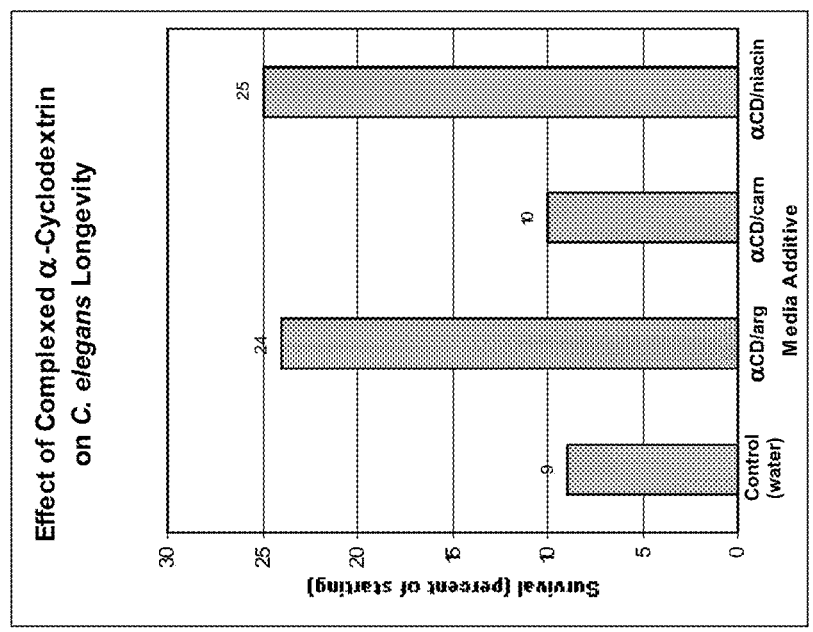
FIG. 16 shows a comparison of nematode longevity in media variably including cyclodextrin inclusion complexes as an active component of hydration according to the present disclosure.

Table 1 shows comparative effects on the germination of wheat seeds of 0.5% w/v α-CD, 0.5% w/v L-arginine (L-Arg), and 0.5% w/v of an α-CD/L-arginine inclusion complex, each dissolved in USA I water. The above-tabulated results indicate that, compared to pure water lacking any additive (control), wheat seed germination rate is much higher in water including 0.5% (w/v) inclusion complex between α-cyclodextrin and L-arginine (αCD/L-Arg inc. complex). In addition, the results in Table 1 indicate that wheat seed germination rate is much higher in water including inclusion complex between α-cyclodextrin and L-arginine (αCD/L-Arg inc. complex) compared to water including 0.5% (w/v) α-cyclodextrin (αCD) as an additive alone, and also compared to water including 0.5% (w/v) L-arginine (L-Arg) as an additive alone. Thus, the results indicate a complex of α-cyclodextrin and L-arginine has a synergistic effect on increasing seed germination rate, which is not shown by either individual component of the complex used as a solitary additive. Results of Table 1 are also shown in FIGS. 11 and 13.

B) Cyclodextrin/Nicotinamide Inclusion Complex Increases Seed Germination.

TABLE 2

Effect of α-cyclodextrin and nicotinamide on wheat seed germination rate

| Days | Control (water) | α-Cyclodextrin, 0.5% | nicotinamide, 0.5% | α-CD/nicot. inc. complex |
|---|---|---|---|---|
| 0 | 2 | 0 | 0 | 0 |
| 1 | 9 | 11 | 0 | 0 |
| 2 | 50 | 18 | 4 | 65 |
| 3 | 62 | 68 | 10 | 88 |
| 4 | 90 | 92 | 60 | 100 |

Table 2 shows comparative effects on the germination of wheat seeds of 0.5% w/v α-cyclodextrin, 0.5% w/v nicotinamide, and 0.5% w/v of an α-cyclodextrin/nicotinamide inclusion complex (αCD/nicot. inc. Complex), each dissolved in USA I water. The above-tabulated results indicate that, compared to pure water lacking any additive (control), wheat seed germination rate is much higher in water including inclusion complex between α-cyclodextrin and nicotinamide. In addition, the results in Table 2 indicate that wheat seed germination rate is much higher in water including inclusion complex between α-cyclodextrin and nicotinamide (αCD/nicot. inc. complex) compared to water including α-cyclodextrin (αCD) as an additive alone, and also compared to water including nicotinamide as an additive alone. Thus, the results indicate that when used as an inclusion complex, α-cyclodextrin and nicotinamide have a synergistic biological activity that significantly increases seed germination rate. Such biological activity was not demonstrated by either individual component of the complex used as a solitary additive. Results of Table 2 are also shown in FIGS. 12 and 13.

Figure 12:
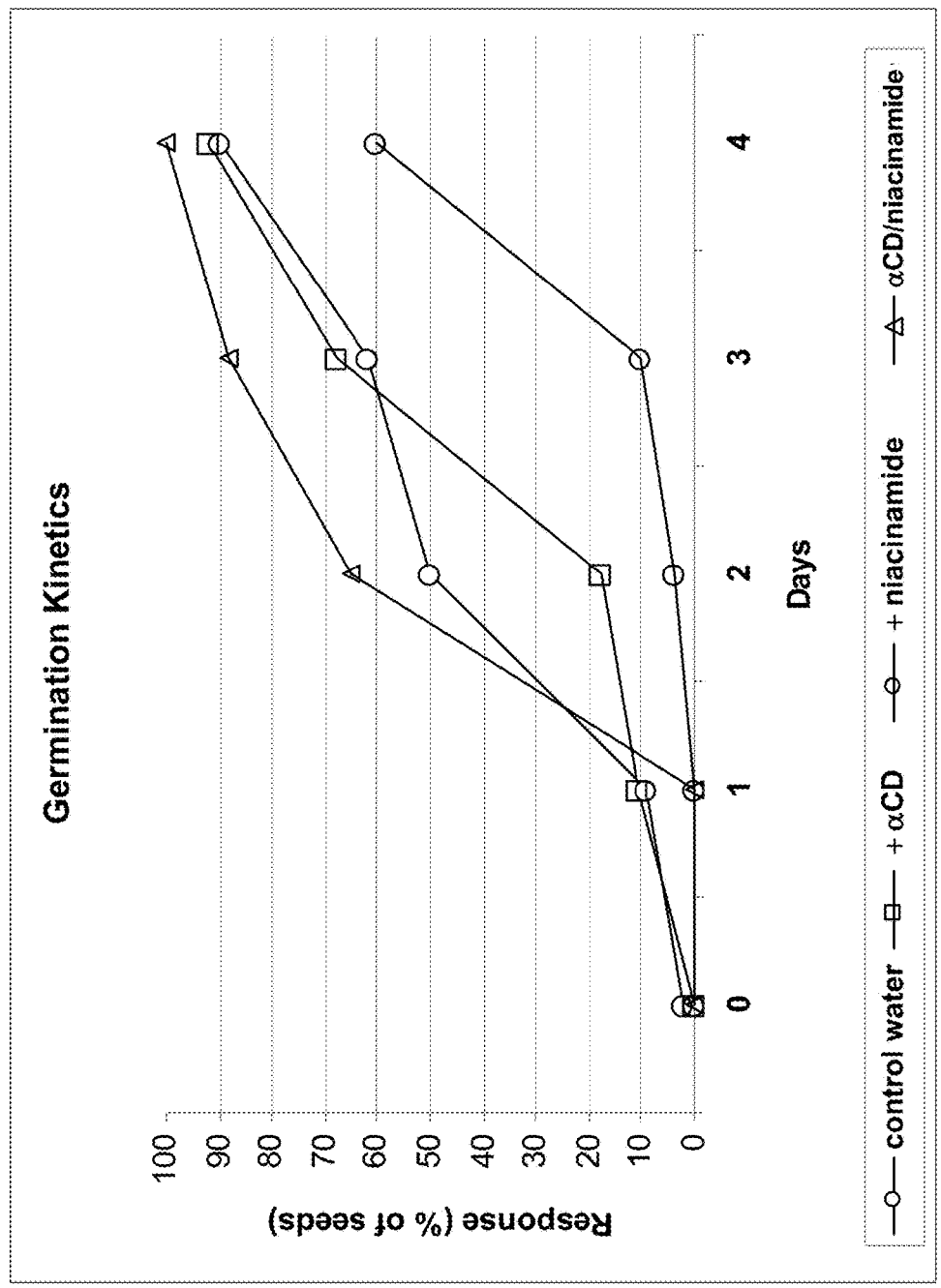
FIG. 12 shows a comparison of seed germination kinetics in water variably including a cyclodextrin, a vitamin, and a cyclodextrin/vitamin inclusion complex.

C) Qualitatively similar results as those reported in Tables 1 and 2, and FIGS. 11-13, were obtained using USA II and BP I water for germination. Thus, in particular, cyclodextrin inclusion complexes containing L-arginine, or alternatively containing nicotinamide, when dissolved in USA II or alternatively in BP I water, each significantly increased wheat seed germination rate, as shown above using USA I water.

D) Lengths of sprouts (rate of sprout growth during germination) did not differ between conditions within a statistically significant confidence interval ($P<0.05$). This result indicates that cyclodextrins, and particularly cyclodextrin inclusion complexes, may be used selectively as active components of cellular hydration to promote a rate of seed germination without necessarily also affecting a sprout growth rate.

Example 4

Lifespan Extension of *C. elegans* in Hydration Modified Water

*C. elegans* nematodes were grown in petri-type dishes containing normal nutrient liquid media prepared alternatively with USA I water (described in Example 2) lacking any further additive component (control) or the same water supplemented with a parent α-, β-, or γ-cyclodextrin, and/or a bioactive agent, as an active component of cellular hydration. Fifty±3 worms were transferred to each dish. Each condition was repeated in triplicate. Experiments were repeated for USA II and BP I waters described in Example 2.

Water Additives:
A. Addition of parent α-, β- and γ-cyclodextrins.
B. Addition of L-arginine and nicotinamide.
C. Addition of inclusion complexes of cyclodextrins with L-arginine and nicotinamide.

Observations:
The results recorded are displayed below in Tables 3-5 and further presented in FIGS. 14-18.

TABLE 3

Effect of cyclodextrins on *C. elegans* longevity

| | Animals alive, % of initial (N = 50) | | | |
|---|---|---|---|---|
| Life Span (days) | Control (water) | α-Cyclodextrin, 0.1% | β-Cyclodextrin, 0.1% | γ-Cyclodextrin, 0.1% |
| 10 | 92 | 100 | 100 | 100 |
| 15 | 10 | 20 | 18 | 13 |
| 18 | 0 | 2 | 0 | 2 |

Table 3 reports the percentage of animals surviving to midlife (10 days), advanced age (15 days) and old age (18 days), in media variably containing a parent α-, β-, and γ-cyclodextrin as an active component of cellular hydration. In this example, parent cyclodextrins were added at a concentration of 0.1% w/v to nutritive media dissolved in USA I water.

Consistent with all previous studies, normal *C. elegans* animals in the present example survived two weeks in normal media. Each of the parent cyclodextrins markedly increased C. elegans survival (percentage alive) at advanced lifespan ages (days 10-15). Further, α-cyclodextrin and γ-cyclodextrins significantly increased the number of animals surviving to old ages, i.e., after day 15. The results are also represented graphically in FIG. 14, which compares the cumulative percentages of animals surviving to 15 and 18 days in media containing each additive parent cyclodextrin. The results show parent cyclodextrins, particularly α- and β-cyclodextrin, may be used as an active component of cellular hydration to improve biological function in a live animal.

Biological mechanisms supporting advanced aging may include improvement of broad spectrum cellular activity during aging, or alternatively by selectively activating slow-aging cellular activity pathways. Clathrate-induced increases in water structure, hydration of cellular components, and diffusivity of bioactive cellular components, including inter- and intra-cellular signals, may all contribute to the overall effects of cyclodextrins on organism survival.

TABLE 4

Effect of chemically-modified cyclodextrins C. elegans longevity

| Life Span (days) | Animals alive, % of initial (N = 50) | | | |
|---|---|---|---|---|
| | Control (water) | HP-β-Cyclodextrin | Carboxymethyl-β-Cyclodextrin | Quaternaryammonium-β-Cyclodextrin |
| 10 | 90 | 96 | 94 | 98 |
| 15 | 8 | 17 | 11 | 13 |
| 18 | 0 | 0 | 0 | 2 |

Table 4 reports the percentage of animals surviving to midlife (10 days), advanced age (15 days) and old age (18 days), in media variably containing a derivatized α-, β-, and γ-cyclodextrin as an active component of cellular hydration. In this example, derivatized cyclodextrins were added at 0.1% w/v to nutritive media dissolved in USA I water.

HP—, carboxymethyl-, and quaternaryammonium-derivatives of β-cyclodextrin had only slight effect on the initial survival of C. elegans to 10 days, as listed in Table 4. In contrast, significant increases in survival were observed at advanced ages (15 days), but not at old ages (18 days). The results are also shown graphically in FIG. 15, which compares the cumulative percentages of animals surviving to 15 and 18 days in media containing each additive derivatized cyclodextrin. The results indicate derivatized cyclodextrins may be used as an active component of cellular hydration to improve biological function in a live animal.

TABLE 5

Effect of cyclodextrin complexes on C. elegans longevity

| Life Span (days) | Animals alive, % of initial (N = 50) | | | |
|---|---|---|---|---|
| | Control (water) | α-CD/L-Arg | α-CD/L-carnitine | α-CD/nicotinamide |
| 10 | 94 | 97 | 98 | 100 |
| 14 | 9 | 22 | 10 | 24 |
| 18 | 0 | 2 | 0 | 3 |

Table 5 reports the percentage of animals surviving to midlife (10 days), advanced age (14 days), and old age (18 days), in nutritive media dissolved in USA I water variably supplemented with a cyclodextrin inclusion complex at 0.1% w/v, as an active component of cellular hydration. In this example, inclusion complexes contained α-cyclodextrin and a bioactive agent, particularly L-arginine, L-carnitine, or niacinamide.

As in previous examples, C. elegans animals in unsupplemented media survived two weeks. α-Cyclodextrin complexes with L-arginine and niacinamide more than doubled C. elegans survival at advanced ages (day 14), and further permitted a small but significant number of animals to survive to an old age, to which no animal survived in nutritive media alone. In contrast, α-cyclodextrin complexes with L-carnitine had little or no significant effect on C. elegans survival. Similarly, L-arginine and nicotinamide added alone to the culture media without α-cyclodextrin had little effect on C. elegans survival. Results are also shown graphically in FIG. 16, which compares the cumulative percentages of animals surviving to 14 and 18 days in media containing each cyclodextrin inclusion complex as an additive. The results indicate α-cyclodextrin inclusion complexes, particularly complexes with L-arginine and niacinamide, may be used as an active component of cellular hydration to improve biological function in a live animal.

Figure 17:
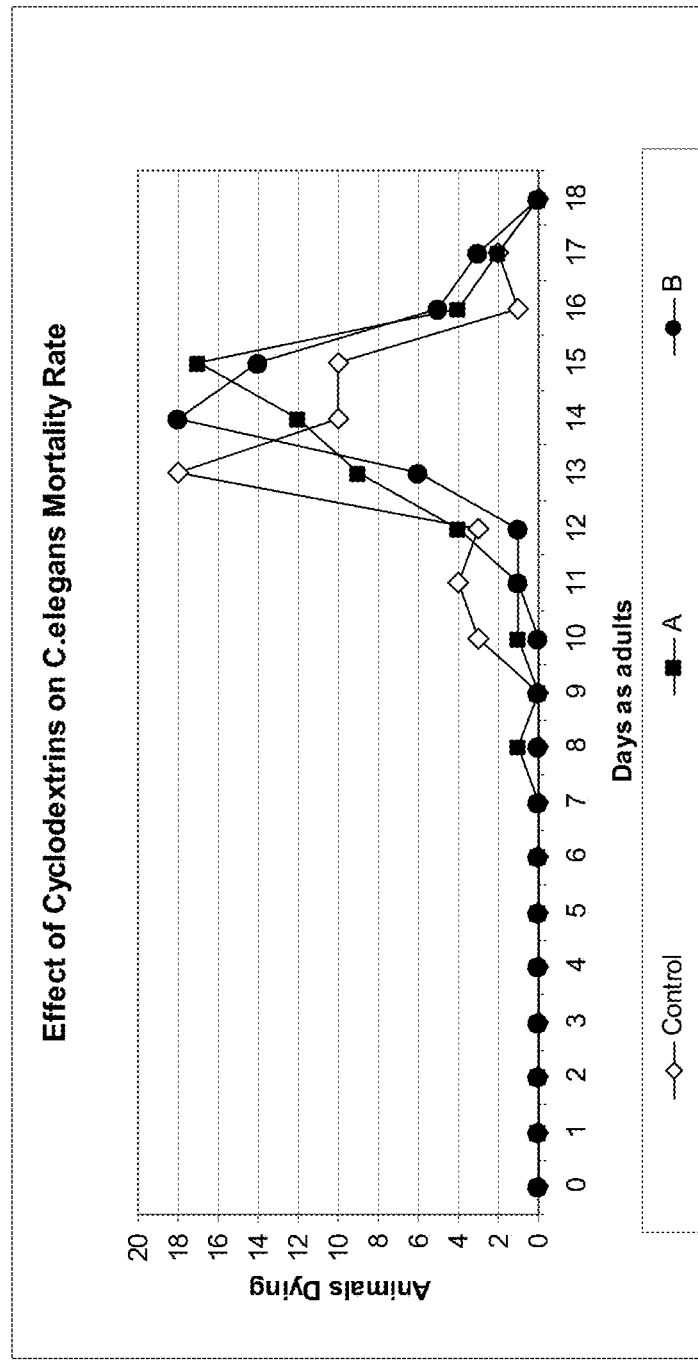
FIG. 17 shows nematode mortality frequency in media with and without a cyclodextrin inclusion complex included as an active component of hydration according to the present disclosure.

As further shown in FIG. 17, an inclusion complex of α-cyclodextrin and L-arginine (data series A; 1:1 complex, dissolved at 0.1% w/v in media made with USA I water), and an inclusion complex of α-cyclodextrin and niacinamide (data series B; 1:1 complex, dissolved at 0.1% w/v in media made with USA I water) can decrease the mortality rate of C. elegans worms. FIG. 17 shows the number of animals dying on each day for each media condition, wherein the control data series is media made with USA I water and lacking a further additive or supplement. The results show complexed forms of α-cyclodextrin may be used as an active component of cellular hydration to retard mortality of a live animal.

FIG. 18 alternatively represents the data of FIG. 17 as a survival curve for animals growing in normal media using USA I water (Control), or alternatively in media supplemented with a 1:1 inclusion complex of α-cyclodextrin and L-arginine (Sample 1); or in media supplemented with a 1:1 inclusion complex of cyclodextrin and niacinamide (Sample 2). Thus, the delay in mortality shown in FIG. 17 results in an older age of survival, the average age of survival (50% survival) increasing from nearly 13 days in normal media to nearly 14 days in media including a cyclodextrin inclusion complex as an active component of cellular hydration, which represents an 8% increase in lifespan.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

What is claimed is:

1. A composition for increasing an activity of a biological cell system comprising:
   a carbohydrate clathrate component that includes cyclodextrin, in a concentration of 0.1-5% w/v, and is effective to increase hydration by increasing the H-bonded structure of water;
   a hydration-effecting agent that is chosen from the group consisting of a vitamin, an amino acid or an amine;
   a complex-forming compound, in a concentration of 5-8% w/v;
   an aqueous liquid component chosen from the group consisting of still and carbonated aqueous liquids;
   wherein an inclusion complex is formed with at least 25% of the clathrate component, the complex-forming compound, and the hydration-effecting agent; and
   wherein the inclusion complex includes the capability of increasing an activity of a biological cell system by increasing the hydration of one or more components of that cell system.

2. The composition of claim 1, wherein the hydration-effecting agent increases an activity of a biological cell system by increasing the hydration of one or more components of that cell system.

3. The composition of claim 1, further including a flavorant that is chosen from the group consisting of apple, apricot, banana, grape, blackcurrant, raspberry, peach, pear, pineapple, plum, orange, and vanilla flavorants.

4. The composition of claim 1, further including a colorant that is chosen from the group consisting of betalains, betacyanins, betaxanthins, vulgaxanthin, miraxanthin, portulaxanthin, indicaxanthin, anthocyanidins, aurantinidin, cyanidin, delphinidin, europinidin, luteolinidin, pelargonidin, malvidin, peonidin, petunidin, rosinidin, corresponding anthocyanins or glucosides of anthocyanidins, turmeric type colorants, phenolic curcuminoids, curcumin, demethoxycurcumin and bisdemethoxycurcumin.

5. The composition of claim 1, wherein the hydration-effecting agent further includes a vitamin that is chosen from the group consisting of nicotinamide (vitamin $B_3$), niacinamide, niacin, pyridoxal hydrochloride (vitamin $B_6$), ascorbic acid, edible ascorbyl esters, riboflavin, pyridoxine, thiamine, vitamin $B_9$, folic acid, folate, pteroyl-L-glutamic acid, pteroyl-L-glutamate, salts thereof, and mixtures thereof.

6. The composition of claim 1, wherein the hydration-effecting agent includes an amino acid that is chosen from the group consisting of aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, salts thereof, mixtures thereof, and N-alkyl $C_1$-$C_3$ and N-acylated $C_1$-$C_3$ derivatives of these amino acids, and mixtures of any of the amino acids or derivatives thereof.

7. The composition of claim 1, formed as a beverage.

8. The composition of claim 7, wherein the hydration-effecting agent is also the complex-forming compound.

* * * * *